(12) United States Patent
Sonoda et al.

(10) Patent No.: US 9,085,626 B2
(45) Date of Patent: Jul. 21, 2015

(54) FGFR1 AGONISTS AND METHODS OF USE

(75) Inventors: Junichiro Sonoda, San Mateo, CA (US);
Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 45 days.

(21) Appl. No.: 13/472,352

(22) Filed: May 15, 2012

(65) Prior Publication Data

US 2012/0294861 A1    Nov. 22, 2012

Related U.S. Application Data

(60) Provisional application No. 61/536,936, filed on Sep. 20, 2011, provisional application No. 61/486,731, filed on May 16, 2011.

(51) Int. Cl.
| | | |
|---|---|---|
| *A61K 39/395* | (2006.01) | |
| *C12N 15/13* | (2006.01) | |
| *C07K 16/28* | (2006.01) | |
| *A61K 39/00* | (2006.01) | |

(52) U.S. Cl.
CPC ............. *C07K 16/2863* (2013.01); *C07K 16/28* (2013.01); *A61K 2039/505* (2013.01); *C07K 2317/31* (2013.01); *C07K 2317/34* (2013.01); *C07K 2317/35* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,531,304 B2 * | 5/2009 | Bange et al. ................ | 435/6.11 |
| 2007/0293430 A1 | 12/2007 | Frye et al. | |
| 2007/0299007 A1 | 12/2007 | Frye et al. | |
| 2012/0059047 A1 | 3/2012 | Prins et al. | |
| 2012/0121609 A1 | 5/2012 | Sun et al. | |

FOREIGN PATENT DOCUMENTS

| | | |
|---|---|---|
| WO | 01/04160 | 1/2001 |
| WO | 2005/037325 | 4/2005 |
| WO | 2005/066211 A2 | 7/2005 |
| WO | 2010/042747 | 4/2010 |
| WO | 2011/071783 | 6/2011 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Atwell et al., "Stable heterodimers from remodeling the domain interface of a homodimer using a phage display library" J. Mol. Biol. 270(1):26-35 (1997).
Berglund et al., "Fibroblast growth factor 21 controls gylcemia via regulation of hepatic glucose flux and insulin sensitivity" Endocrinology 150(9):4084-4093 (2009).
Chau et al., "Fibroblast growth factor 21 regulates energy metabolism by activating the AMPK-SIRT1-PGC-1δ pathway" PNAS 107(28):12553-12558 (2010).
Coskun et al., "Fibroblast growth factor 21 corrects obesity in mice" Endocrinology 149 (2):6018-6027 (2008).

(Continued)

*Primary Examiner* — Brian J Gangle
*Assistant Examiner* — Andrea McCollum
(74) *Attorney, Agent, or Firm* — Grant Kalinowski

(57) ABSTRACT

The invention provides FGFR1 agonists, including agonistic anti-FGFR1 antibodies, and methods of using the same.

14 Claims, 29 Drawing Sheets

(56) References Cited

OTHER PUBLICATIONS

Fon Tacer et al., "Research resource: Comprehensive expression atlas of the fibroblast growth factor system in adult mouse" Mol. Endocrinol 24(10):2050-2064 ( 2010).

Hart et al., "Attenuation of FGF signaling in mouse β-cells lead to diabetes" Nature 408:864 ( 2000).

Hondares et al., "Hepatic FGF21 Expression Induced at Birth via PPARα in Response to Milk Intake and Contributes to Thermogenic Activation of Neonatal Brown Fat" Cell Metabolism 11:206-212 ( 2010).

Inagaki et al., "Inhibition of growth hormone signaling by the fasting-induced hormone FGF21" Cell Metabolism 8:77-83 ( 2008).

Kharitonenkov et al., "FGF-21 as a novel metabolic regulator" J Clin Invest. 115(6):1627-35 (Jun. 2005).

Kharitonenkov et al., "FGF21 reloaded challenges of a rapidly growing field" Trends in Endocrinology and Metabolism 22(3):81 ( 2011).

Kurosu et al., "Tissue-specific expression of βKlotho and fibroblast growth factor (FGF) receptor isoforms determines metabolic activity of FGF19 and FGF21." J Biol Chem. 282(37):26687-26695 (Sep. 2007).

Li et al., "Inhibition of lipolysis may contribute to the acute regulation of plasma FFA and glucose by FGF21 in *ob/ob* mice" FEBS Letters 583:3230-3234 ( 2009).

Ogawa et al., "βKlotho is required for metabolic activity of fibroblast growth factor 21" PNAS 104(18):7432-7437 ( 2007).

Potthoff et al., "FGF21 induces PGC-1α and regulated carbohydrate and fatty acid metabolism during the adaptive starvation response" PNAS 106(26):10853-10858 ( 2009).

Sun et al., "Monoclonal antibody antagonists of hypothalamic FGFR1 cause potent but reversible hypophagia and weight loss in rodents and monkeys" Am. J. Physiol. Endocrinol. Metab 292:E964-E976 ( 2007).

Suzuki et al., "βKlotho is required for fibroblast growth factor (FGF) 21 signaling through FGF receptor (FGFR) 1c and FGFR3c" Molec. Endocrin. 22(4):1006-1014 ( 2008).

Wente et al., "Fibroblast growth factor-21 improves pancreatic beta-cell function and survival by activation of extracellular signal-regulated kinase 1/2 and Akt signaling pathways" Diabetes 55:2470-2478 ( 2006).

Wu et al., "Amelioration of type 2 diabetes by antibody-mediated activation of fibroblast growth factor receptor 1" Science Translational Medicine 3:113ra-126 ( 2011).

Xu et al., "Acute glucose-lowering and insulin-sensitizing action of FGF21 in insulin-resistant mouse models—association with liver and adipose tissue effects" America Journal of Physiology—Endocrinology and Metabolism 297:E1105-E1114 ( 2009).

Xu et al., "Fibroblast growth factor 21 reverses hepatic steatosis, increase energy expenditure, and improves insulin sensitivity in diet-induced obese mice" Diabetes 58:250-259 ( 2009).

\* cited by examiner

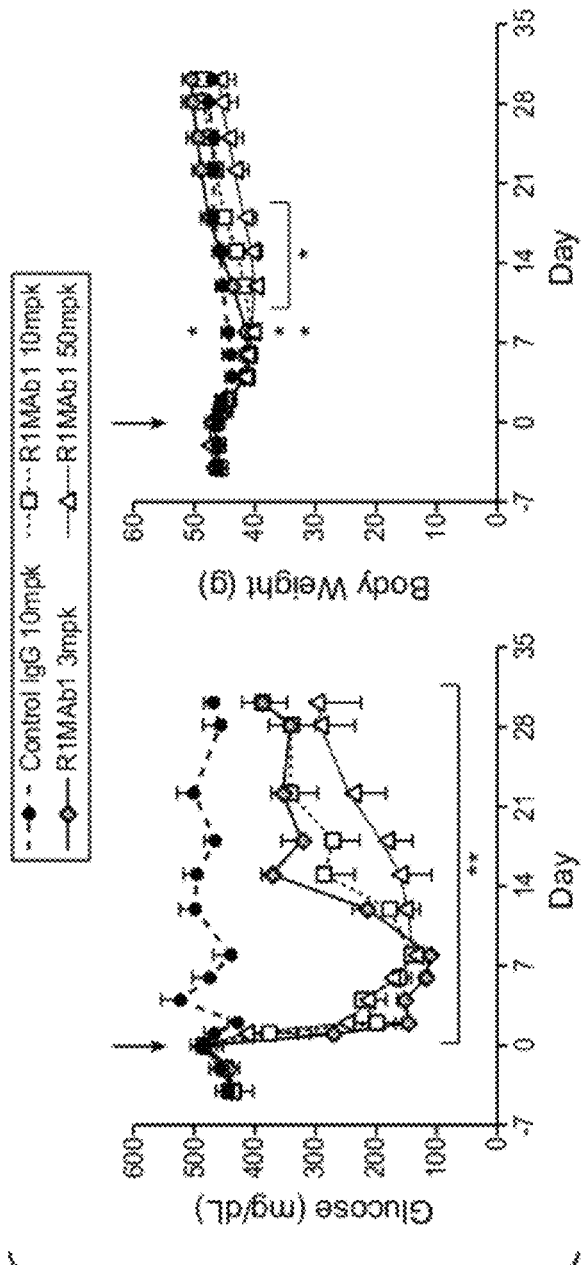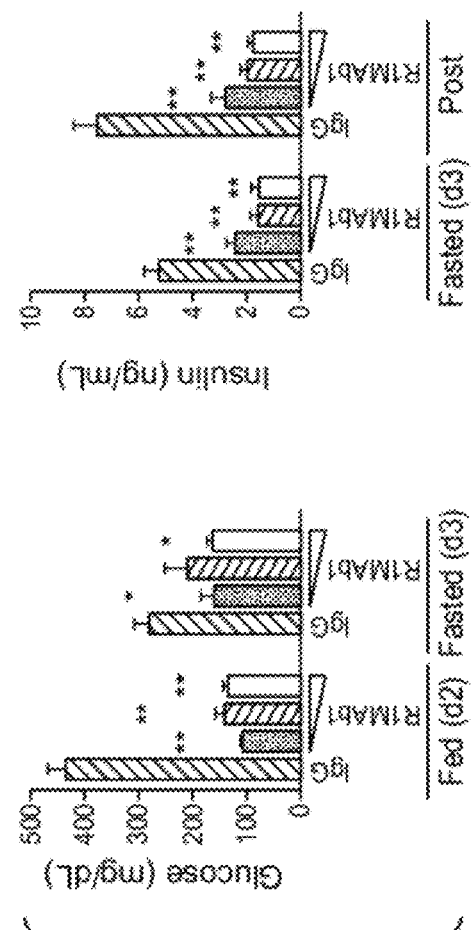
FIG. 2A
FIG. 2B

```
    161                                                              212
...MEKKLHAVPAAKTVKFKCPSSGTPNPTLRWLKNGKEFKPDHRIGGYKVRYATW...
FGFR1:KLHAVPAAKTVKFKCP(#26)              FKPDHRIGGYKVRY(#28)
FGFR2:RLHAVPAANTVKFRCP                   FKDEHRIGGYKVRN
FGFR3:KLLAVPAANTVRFRCP                   FRGEHRIGGIKLRH
FGFR4:KLHAVPAGNTVKFRCP                   FHGENRIGGIRLRH
```
FIG. 17B
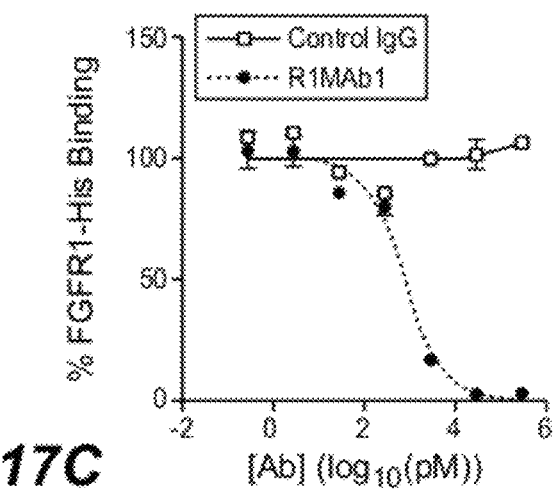
FIG. 17C
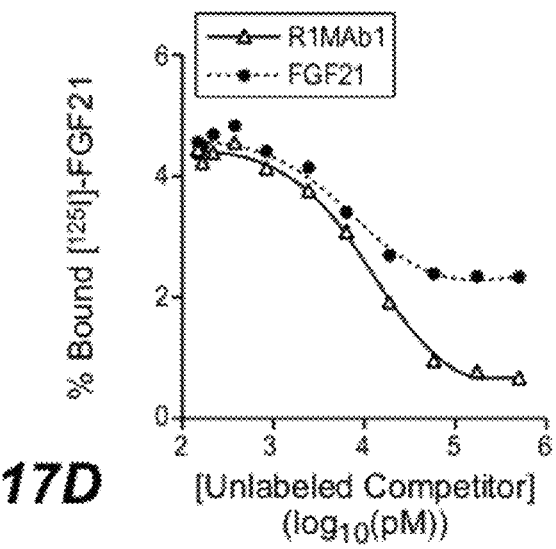
FIG. 17D

SEQUENCE LISTING

<160> NUMBER OF SEQ ID NOS: 63

<210> SEQ ID NO 1
<211> LENGTH: 229
<212> TYPE: PRT
<213> ORGANISM: Homo sapiens

<400> SEQUENCE: 1

```
Asn Thr Lys Pro Asn Pro Val Ala Pro Tyr Trp Thr Ser Pro Glu Lys
1               5                   10                  15

Met Glu Lys Lys Leu His Ala Val Pro Ala Ala Lys Thr Val Lys Phe
                20                  25                  30

Lys Cys Pro Ser Ser Gly Thr Pro Asn Pro Thr Leu Arg Trp Leu Lys
            35                  40                  45

Asn Gly Lys Glu Phe Lys Pro Asp His Arg Ile Gly Gly Tyr Lys Val
        50                  55                  60

Arg Tyr Ala Thr Trp Ser Ile Ile Met Asp Ser Val Val Pro Ser Asp
65                  70                  75                  80

Lys Gly Asn Tyr Thr Cys Ile Val Glu Asn Glu Tyr Gly Ser Ile Asn
                85                  90                  95

His Thr Tyr Gln Leu Asp Val Val Glu Arg Ser Pro His Arg Pro Ile
            100                 105                 110

Leu Gln Ala Gly Leu Pro Ala Asn Lys Thr Val Ala Leu Gly Ser Asn
        115                 120                 125

Val Glu Phe Met Cys Lys Val Tyr Ser Asp Pro Gln Pro His Ile Gln
    130                 135                 140

Trp Leu Lys His Ile Glu Val Asn Gly Ser Lys Ile Gly Pro Asp Asn
145                 150                 155                 160

Leu Pro Tyr Val Gln Ile Leu Lys His Ser Gly Ile Asn Ser Ser Asp
                165                 170                 175

Ala Glu Val Leu Thr Leu Phe Asn Val Thr Glu Ala Gln Ser Gly Glu
            180                 185                 190

Tyr Val Cys Lys Val Ser Asn Tyr Ile Gly Glu Ala Asn Gln Ser Ala
        195                 200                 205

Trp Leu Thr Val Thr Arg Pro Val Ala Lys Ala Leu Glu Glu Arg Pro
    210                 215                 220
```

Ala Val Met Thr Ser
225

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Trp Ile Ser Trp Val Pro Gly Lys Gly Leu Glu Trp Val Gly Glu Ile
        35                  40                  45

Asp Pro Tyr Asp Gly Asp Thr Tyr Tyr Ala Asp Ser Val Lys Gly Arg
    50                  55                  60

Phe Thr Ile Ser Ala Asp Thr Ser Lys Asn Leu Gln Met Asn Ser Leu
65                  70                  75                  80

Arg Ala Glu Asp Thr Ala Val Tyr Tyr Cys Ala Ser Ser Gly Tyr Gly
                85                  90                  95

Gly Ser Asp Tyr Ala Met Asp Tyr Trp Gly Gln
            100                 105

<210> SEQ ID NO 3
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Asn
            20                  25                  30

Tyr Ile His Trp Val Pro Gly Lys Gly Leu Glu Trp Val Ala Asp Ile
        35                  40                  45

Tyr Pro Asn Asp Gly Asp Thr Asp Tyr Ala Asp Ser Val Lys Gly Arg
    50                  55                  60

Phe Thr Ile Ser Ala Asp Thr Ser Lys Asn Leu Gln Met Asn Ser Leu
65                  70                  75                  80

Arg Ala Glu Asp Thr Ala Val Tyr Tyr Cys Ala Arg Glu His Phe Asp
                85                  90                  95

Ala Trp Val His Tyr Tyr Val Met Asp Tyr Trp Gly Gln
            100                 105

<210> SEQ ID NO 4
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Gly

```
                1               5                  10                 15
            Ser Leu Arg Leu Ser Cys Ala Ala Ser Gly Phe Thr Phe Thr Ser Asn
                            20                  25                  30

Trp Ile Ser Trp Val Pro Gly Lys Gly Leu Glu Trp Val Ala Glu Ile
                            35                  40                  45

Asp Pro Tyr Asp Gly Ala Thr Asp Tyr Ala Asp Ser Val Lys Gly Arg
                            50                  55                  60

Phe Thr Ile Ser Ala Asp Thr Ser Lys Asn Leu Gln Met Asn Ser Leu
            65                  70                  75                  80

Arg Ala Glu Asp Thr Ala Val Tyr Tyr Cys Ala Thr Gly Thr Asp Val
                            85                  90                  95

Met Asp Tyr Trp Gly Gln
                            100

<210> SEQ ID NO 5
<211> LENGTH: 227
<212> TYPE: PRT
<213> ORGANISM: Homo sapiens

<400> SEQUENCE: 5

Asn Thr Lys Pro Asn Pro Val Ala Pro Tyr Trp Thr Ser Pro Glu Lys
            1               5                  10                  15

Met Glu Lys Lys Leu His Ala Val Pro Ala Ala Lys Thr Val Lys Phe
                            20                  25                  30

Lys Cys Pro Ser Ser Gly Thr Pro Asn Pro Thr Leu Arg Trp Leu Lys
                            35                  40                  45

Asn Gly Lys Glu Phe Lys Pro Asp His Arg Ile Gly Gly Tyr Lys Val
                            50                  55                  60

Arg Tyr Ala Thr Trp Ser Ile Ile Met Asp Ser Val Val Pro Ser Asp
            65                  70                  75                  80

Lys Gly Asn Tyr Thr Cys Ile Val Glu Asn Glu Tyr Gly Ser Ile Asn
                            85                  90                  95

His Thr Tyr Gln Leu Asp Val Val Glu Arg Ser Pro His Arg Pro Ile
                            100                 105                 110

Leu Gln Ala Gly Leu Pro Ala Asn Lys Thr Val Ala Leu Gly Ser Asn
                            115                 120                 125

Val Glu Phe Met Cys Lys Val Tyr Ser Asp Pro Gln Pro His Ile Gln
                            130                 135                 140

Trp Leu Lys His Ile Glu Val Asn Gly Ser Lys Ile Gly Pro Asp Asn
            145                 150                 155                 160

Leu Pro Tyr Val Gln Ile Leu Lys Thr Ala Gly Val Asn Thr Thr Asp
                            165                 170                 175

Lys Glu Met Glu Val Leu His Leu Arg Asn Val Ser Phe Glu Asp Ala
                            180                 185                 190

Gly Glu Tyr Thr Cys Leu Ala Gly Asn Ser Ile Gly Leu Ser His His
                            195                 200                 205

Ser Ala Trp Leu Thr Val Leu Glu Ala Leu Glu Glu Arg Pro Ala Val
                            210                 215                 220

Met Thr Ser
            225

<210> SEQ ID NO 6
<211> LENGTH: 108
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Phe Thr Phe Thr Ser Thr Trp Ile Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Phe Thr Phe Ser Asn Asn Tyr Ile His
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Phe Thr Phe Thr Ser Asn Trp Ile Ser
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Glu Ile Asp Pro Tyr Asp Gly Asp Thr Tyr Ala Asp Ser Val
1               5                   10                  15

Lys Gly

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Ile Asp Pro Tyr Asp Gly Asp Thr Tyr Ala Asp Ser Val Lys
1               5                   10                  15

Gly

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Asp Ile Tyr Pro Asn Asp Gly Asp Thr Tyr Ala Asp Ser Val
1               5                   10                  15

Lys Gly

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ile Tyr Pro Asn Asp Gly Asp Thr Asp Tyr Ala Asp Ser Val Lys
1               5                   10                  15

Gly

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Glu Ile Asp Pro Tyr Asp Gly Ala Thr Asp Tyr Ala Asp Ser Val
1               5                   10                  15

Lys Gly

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Glu Ile Asp Pro Tyr Asp Gly Ala Thr Asp Tyr Ala Asp Ser Val Lys
1               5                   10                  15
Gly

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ser Gly Tyr Gly Gly Ser Asp Tyr Ala Met Asp Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Gly Tyr Gly Gly Ser Asp Tyr Ala Met Asp Tyr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu His Phe Asp Ala Trp Val His Tyr Tyr Val Met Asp Tyr
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Gly Thr Asp Val Met Asp Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Thr Asp Val Met Asp Tyr
1               5

<210> SEQ ID NO 21
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Ser Gln Asp Val Ser Thr Ala Val Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ala Ser Phe Leu Tyr Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gln Ser Tyr Thr Thr Pro Pro Thr
1               5

<210> SEQ ID NO 24
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala or Gly
<220> FEATURE:
<221> NAME/KEY: MOD_RES
<222> LOCATION: (2)..(2)
<223> OTHER INFORMATION: Asp or Glu
<220> FEATURE:
<221> NAME/KEY: MOD_RES
<222> LOCATION: (4)..(4)
<223> OTHER INFORMATION: Asp or Tyr
<220> FEATURE:
<221> NAME/KEY: MOD_RES
<222> LOCATION: (6)..(6)
<223> OTHER INFORMATION: Asn or Tyr
<220> FEATURE:
<221> NAME/KEY: MOD_RES
<222> LOCATION: (9)..(9)
<223> OTHER INFORMATION: Ala or Asp
<220> FEATURE:
<221> NAME/KEY: MOD_RES
<222> LOCATION: (11)..(11)
<223> OTHER INFORMATION: Asp or Tyr

<400> SEQUENCE: 24

Xaa Xaa Ile Xaa Pro Xaa Asp Gly Xaa Thr Xaa Tyr Ala Asp Ser Val
1               5                   10                  15

Lys Gly
```

```
<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Glu
<220> FEATURE:
<221> NAME/KEY: MOD_RES
<222> LOCATION: (3)..(3)
<223> OTHER INFORMATION: Asp or Tyr
<220> FEATURE:
<221> NAME/KEY: MOD_RES
<222> LOCATION: (5)..(5)
<223> OTHER INFORMATION: Asn or Tyr
<220> FEATURE:
<221> NAME/KEY: MOD_RES
<222> LOCATION: (8)..(8)
<223> OTHER INFORMATION: Ala or Asp
<220> FEATURE:
<221> NAME/KEY: MOD_RES
<222> LOCATION: (10)..(10)
<223> OTHER INFORMATION: Asp or Tyr

<400> SEQUENCE: 25

Xaa Ile Xaa Pro Xaa Asp Gly Xaa Thr Xaa Tyr Ala Asp Ser Val Lys
1               5                   10                  15

Gly

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Asn or Ser
<220> FEATURE:
<221> NAME/KEY: MOD_RES
<222> LOCATION: (7)..(7)
<223> OTHER INFORMATION: Asn or Thr
<220> FEATURE:
<221> NAME/KEY: MOD_RES
<222> LOCATION: (8)..(8)
<223> OTHER INFORMATION: Trp or Tyr
<220> FEATURE:
<221> NAME/KEY: MOD_RES
<222> LOCATION: (10)..(10)
<223> OTHER INFORMATION: His or Ser

<400> SEQUENCE: 26

Gly Phe Thr Phe Xaa Xaa Xaa Xaa Ile Xaa
1               5                   10

<210> SEQ ID NO 27
<211> LENGTH: 53
<212> TYPE: PRT
<213> ORGANISM: Homo sapiens

<400> SEQUENCE: 27

Met Glu Lys Lys Leu His Ala Val Pro Ala Ala Lys Thr Val Lys Phe
```

```
                1               5                  10                  15
Lys Cys Pro Ser Ser Gly Thr Pro Asn Pro Thr Leu Arg Trp Leu Lys
                    20                  25                  30

Asn Gly Lys Glu Phe Lys Pro Asp His Arg Ile Gly Gly Tyr Lys Val
            35                  40                  45

Arg Tyr Ala Thr Trp
        50

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Leu His Ala Val Pro Ala Ala Lys Thr Val Lys Phe Lys Cys Pro
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Phe Lys Pro Asp His Arg Ile Gly Gly Tyr Lys Val Arg Tyr
1               5                   10

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Leu His Ala Val Pro Ala Ala Asn Thr Val Lys Phe Arg Cys Pro
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Leu Leu Ala Val Pro Ala Ala Asn Thr Val Arg Phe Arg Cys Pro
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Leu His Ala Val Pro Ala Gly Asn Thr Val Lys Phe Arg Cys Pro
```

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Phe Lys Gln Glu His Arg Ile Gly Gly Tyr Lys Val Arg Asn
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Phe Arg Gly Glu His Arg Ile Gly Gly Ile Lys Leu Arg His
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Phe His Gly Glu Asn Arg Ile Gly Gly Ile Arg Leu Arg His
1               5                   10

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Ser Ser Ser Glu Glu Lys Glu Thr Asp Asn Thr Lys Pro Asn Pro Val
1               5                   10                  15

Ala Pro Tyr

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Pro Val Ala Pro Tyr Trp Thr Ser Pro Glu Lys Met Glu Lys Lys Leu
1               5                   10                  15

His Ala Val

<210> SEQ ID NO 38
<211> LENGTH: 19

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Leu His Ala Val Pro Ala Ala Lys Thr Val Lys Phe Lys Cys Pro
1               5                   10                  15

Ser Ser Gly

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Pro Ser Ser Gly Thr Pro Asn Pro Thr Leu Arg Trp Leu Lys Asn
1               5                   10                  15

Gly Lys Glu

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Asn Gly Lys Glu Phe Lys Pro Asp His Arg Ile Gly Gly Tyr Lys
1               5                   10                  15

Val Arg Tyr

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Lys Val Arg Tyr Ala Thr Trp Ser Ile Ile Met Asp Ser Val Val
1               5                   10                  15

Pro Ser Asp

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Val Pro Ser Asp Lys Gly Asn Tyr Thr Cys Ile Val Glu Asn Glu
1               5                   10                  15

Tyr Gly Ser

<210> SEQ ID NO 43
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asn Glu Tyr Gly Ser Ile Asn His Thr Tyr Gln Leu Asp Val Val Glu
1               5                   10                  15

Arg Ser Pro

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Glu Arg Ser Pro His Arg Pro Ile Leu Gln Ala Gly Leu Pro Ala
1               5                   10                  15

Asn Lys Thr

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Ala Asn Lys Thr Val Ala Leu Gly Ser Asn Val Glu Phe Met Cys
1               5                   10                  15

Lys Val Tyr

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Cys Lys Val Tyr Ser Asp Pro Gln Pro His Ile Gln Trp Leu Lys
1               5                   10                  15

His Ile Glu

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Lys His Ile Glu Val Asn Gly Ser Lys Ile Gly Pro Asp Asn Leu
1               5                   10                  15

Pro Tyr Val
```

```
<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asn Leu Pro Tyr Val Gln Ile Leu Lys Thr Ala Gly Val Asn Thr Thr
1               5                   10                  15

Asp Lys Glu

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Thr Asp Lys Glu Met Glu Val Leu His Leu Arg Asn Val Ser Phe
1               5                   10                  15

Glu Asp Ala

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Phe Glu Asp Ala Gly Glu Tyr Thr Cys Leu Ala Gly Asn Ser Ile
1               5                   10                  15

Gly Leu Ser

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Ile Gly Leu Ser His His Ser Ala Trp Leu Thr Val Leu Glu Ala
1               5                   10                  15

Leu Glu Glu

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Tyr Trp Thr Ser Pro Glu Lys Met Glu Lys Lys Leu His Ala Val Pro
1               5                   10                  15

Ala Ala Lys
```

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Lys Met Glu Lys Lys Leu His Ala Val Pro Ala Ala Lys Thr Val
1               5                   10                  15

Lys Phe Lys

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Ala Ala Lys Thr Val Lys Phe Lys Cys Pro Ser Ser Gly Thr Pro
1               5                   10                  15

Asn Pro Thr

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Phe Lys Cys Pro Ser Ser Gly Thr Pro Asn Pro Thr Leu Arg Trp
1               5                   10                  15

Leu Lys Asn

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Thr Pro Asn Pro Thr Leu Arg Trp Leu Lys Asn Gly Lys Glu Phe
1               5                   10                  15

Lys Pro Asp

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Leu Arg Trp Leu Lys Asn Gly Lys Glu Phe Lys Pro Asp His Arg
1               5                   10                  15

Ile Gly Gly

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Phe Lys Pro Asp His Arg Ile Gly Gly Tyr Lys Val Arg Tyr Ala Thr
1               5                   10                  15

Trp Ser Ile

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Arg Ile Gly Gly Tyr Lys Val Arg Tyr Ala Thr Trp Ser Ile Ile
1               5                   10                  15

Met Asp Ser

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu His Ala Val Pro Ala Ala Lys Thr Val Lys Phe Lys Cys Pro Ser
1               5                   10                  15

Ser

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Val Pro Ala Ala Lys Thr Val Lys Phe Lys Cys Pro Ser Ser Gly
1               5                   10                  15

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Pro Asp His Arg Ile Gly Gly Tyr Lys Val Arg
1               5                   10

<210> SEQ ID NO 63

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Thr Pro Asn Pro Thr Leu Arg Trp Leu Lys Asn
1               5                   10
```

FGFR1 AGONISTS AND METHODS OF USE

CROSS REFERENCE TO RELATED APPLICATIONS

This application claims benefit of priority to U.S. Patent Applications 61/486,731, filed May 16, 2011, and 61/536,936, filed Sep. 20, 2011, the entire contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 27, 2012, is named P4653RUS.txt and is 26,083 bytes in size.

FIELD OF THE INVENTION

The present invention relates to FGFR1 agonists and methods of using the same.

BACKGROUND

The inability to control blood glucose levels underlies a variety of metabolic conditions. Diabetes is a hyperglycemic syndrome that results from a defect in insulin secretion in response to glucose (type 1 and type 2 diabetes) and decreased insulin effectiveness in stimulating skeletal muscle glucose uptake and in restraining hepatic glucose production (type 2 diabetes). Diabetes it a highly prevalent disease and, although therapeutic options are available for some diabetics, there is an urgent need for additional therapies.

Fibroblast growth factor 21 (FGF21) is a member of the endocrine FGF subfamily, that includes FGF19 and FGF23, and it has been identified as a potential disease-modifying agent to reverse obesity and obesity-induced hepatosteatosis and hyperglycemia (see, e.g., Kharitonenkov and Larsen, *Trends Endocrinol. Metab.* 22(3):81-6 (2011); Kharitonenkov et al., *J. Clin. Invest.* 115: 1627-35 (2005); WO 2010/042747). The endocrine FGF21 protein binds to three FGF receptors (FGFRs 1-3), and improves insulin resistance and type 2 diabetes by these receptors together with their membrane bound co-receptor beta-Klotho. However, its development has been hampered by its poor pharmacokinetics and poor understanding of the biological mechanism of action. Anti-FGFR1 antagonist antibodies have also been proposed for the treatment of diabetes (WO 2005/037235). However, the identity of which of the three FGFRs mediates the beneficial metabolic activity of FGF21 has not been discovered.

SUMMARY

The invention is based, in part, on the discovery that activation of FGFR1 ameliorates diabetes. The invention provides FGFR1 agonists, including agonist anti-FGFR1 antibodies and methods of using the same.

In one aspect, the invention provides a method of treating a metabolic disease or condition in an individual, comprising administering to the individual an effective amount of an anti-fibroblast growth factor receptor-1 (FGFR1) agonist, wherein the metabolic disease is selected from the group consisting of: polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), and maturity onset diabetes of the young (MODY). In some embodiments, the FGFR1 agonist does not activate FGFR2 or FGFR3. In some embodiments, the FGFR1 agonist is an anti-FGFR1 antibody. In some embodiments, the anti-FGFR1 antibody has two FGFR1-binding sites, e.g. a full-length antibody or a F(ab')2 fragment. In some embodiments, the antibody binds to peptide #26 KLHAVPAAKTVKFKCP (SEQ ID NO: 28) or peptide #28 FKPDHRIGGYKVRY (SEQ ID NO: 29). In some embodiments, the antibody binds to both peptide #26 and peptide #28. In some embodiments, the anti-FGFR1 antibody binds to both FGFR1b and FGFR1c. In some embodiments, the antibody is a bispecific antibody. In some embodiments, the bispecific antibody also binds to beta-Klotho.

In another aspect, the invention provides an isolated antibody that binds to FGFR1, wherein the antibody is an agonist of FGFR1 activity. In some embodiments, the antibody is not an agonist of FGFR2 or FGFR3. In some embodiments, the antibody is a monoclonal antibody. In some embodiments, the antibody is a human, humanized, or chimeric antibody. In some embodiments, the antibody comprises (a) HVR-H3 comprising an amino acid sequence selected from the group consisting of SSGYGGSDYAMDY (SEQ ID NO: 16), SGYGGSDYAMDY (SEQ ID NO: 17), EHFDAWVHYYVMDY (SEQ ID NO: 18), TGTDVMDY (SEQ ID NO: 19), and GTDVMDY (SEQ ID NO: 20), (b) HVR-L3 comprising the amino acid sequence QQSYTTPPT (SEQ ID NO: 23), and (c) HVR-H2 comprising an amino acid sequence selected from the group consisting of $X_1X_2IX_3PX_4DGX_5TX_6YADSVKG$, wherein $X_1$ is A or G, $X_2$ is D or E, $X_3$ is D or Y, $X_4$ is N or Y, $X_5$ is A or D, and $X_6$ is D or Y (SEQ ID NO: 24) and $X_1IX_2PX_3DGX_4TX_5YADSVKG$, wherein $X_1$ is D or E, $X_2$ is D or Y, $X_3$ is N or Y, $X_4$ is A or D, and $X_5$ is D or Y (SEQ ID NO: 25). In some embodiments, the antibody comprises (a) HVR-H1 comprising the amino acid sequence $GFTFX_1X_2X_3X_4IX_5$, wherein $X_1$ is S or T, $X_2$ is N or S, $X_3$ is N or T, $X_4$ is W or Y, $X_5$ is H or S (SEQ ID NO: 26), (b) HVR-H2 comprising an amino acid sequence selected from the group consisting of $X_1X_2IX_3PX_4DGX_5TX_6YADSVKG$, wherein $X_1$ is A or G, $X_2$ is D or E, $X_3$ is D or Y, $X_4$ is N or Y, $X_5$ is A or D, and $X_6$ is D or Y (SEQ ID NO: 24) and $X_1IX_2PX_3DGX_4TX_5YADSVKG$, wherein $X_1$ is D or E, $X_2$ is D or Y, $X_3$ is N or Y, $X_4$ is A or D, and $X_5$ is D or Y (SEQ ID NO: 25), and (c) HVR-H3 comprising an amino acid sequence selected from the group consisting of SSGYGGSDYAMDY (SEQ ID NO: 16), SGYGGSDYAMDY (SEQ ID NO: 17), EHFDAWVHYYVMDY (SEQ ID NO: 18), TGTDVMDY (SEQ ID NO: 19), and GTDVMDY (SEQ ID NO: 20). In some embodiments, the antibody comprises (a) HVR-H1 comprising the amino acid sequence GFTFTSTWIS (SEQ ID NO: 7), (b) HVR-H2 comprising an amino acid sequence selected from the group consisting of GEIDPYDGDTYYADSVKG (SEQ ID NO: 10) and EIDPYDGDTYYADSVKG (SEQ ID NO: 11), and (c) HVR-H3 comprising an amino acid sequence selected from the group consisting of SSGYGGSDYAMDY (SEQ ID NO: 16) and SGYGGSDYAMDY (SEQ ID NO: 17). In some embodiments, the antibody comprises (a) HVR-H1 comprising the amino acid sequence GFTFSNNYIH (SEQ ID NO: 8), (b) HVR-H2 comprising an amino acid sequence selected from the group consisting of ADIYPNDGDTDYADSVKG (SEQ ID NO: 12) and DIYPNDGDTDYADSVKG (SEQ ID NO: 13), and (c) HVR-H3 comprising the amino acid sequence EHFDAWVHYYVMDY (SEQ ID NO: 18). In some embodiments, the antibody comprises (a) HVR-H1 comprising the amino acid sequence GFTFTSNWIS (SEQ ID NO: 9), (b) HVR-H2 comprising an amino acid sequence selected from the group consisting of AEIDPYDGATDYADSVKG (SEQ ID NO: 14) and EIDPYDGATDYADSVKG (SEQ ID NO: 15), and (c) HVR-H3 comprising an amino acid sequence selected from the group consisting of TGTDVMDY (SEQ ID NO: 19) and GTDVMDY (SEQ ID NO: 20). In some embodiments, the antibody further comprises (a) HVR-L1 comprising the amino acid sequence RASQDVSTAVA (SEQ ID NO: 21); (b) HVR-L2 comprising the amino acid sequence SASFLYS (SEQ ID NO: 22); and (c) HVR-L3 comprising the amino acid sequence QQSYTTPPT (SEQ ID NO: 23). In some embodiments, the antibody comprises a VH sequence selected from the group consisting of SEQ ID NO: 2, 3 and 4. In some embodiments, the antibody comprises a VL sequence of SEQ ID NO: 6.

In some embodiments, the anti-FGFR1 antibody has two FGFR1-binding sites, e.g. a full-length antibody or a F(ab')2 fragment. In some embodiments, the antibody of the invention is a multispecific antibody. In some embodiments, the antibody also binds to beta-Klotho. In some embodiments, the antibody is an IgG1 antibody. In some embodiments, the invention provides an isolated nucleic acid encoding an antibody of the invention. In some embodiments, the invention provides a host cell comprising the nucleic acid of claim 21. In some embodiments, the invention provides method of producing an antibody comprising culturing the host cell of claim 22 so that the antibody is produced. In some embodiments, the method further comprises recovering the antibody from the host cell.

In some embodiments, the invention provides a pharmaceutical formulation comprising an antibody of the invention and a pharmaceutically acceptable carrier.

In some embodiments, the invention provides an antibody of the invention for use as a medicament. In some embodiments, the antibody of the invention is for use in treating a metabolic disease or condition selected from the group consisting of: polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), and maturity onset diabetes of the young (MODY). In some embodiments, the antibody of the invention is for use in sensitizing an individual to insulin.

In some embodiments, the invention provides use of an antibody of the invention in the manufacture of a medicament. In some embodiments, the medicament is for treatment of a metabolic disease or condition selected from the group consisting of: polycystic ovary syndrome (PCOS), metabolic syndrome (MetS), obesity, non-alcoholic steatohepatitis (NASH), non-alcoholic fatty liver disease (NAFLD), hyperlipidemia, hypertension, type 2 diabetes, non-type 2 diabetes, type 1 diabetes, latent autoimmune diabetes (LAD), and maturity onset diabetes of the young (MODY). In some embodiments, the medicament is for sensitizing an individual to insulin.

In some embodiments, the invention provides a method of treating diabetes in an individual, comprising administering to the individual an effective amount of an antibody of the invention. In some embodiments, the method further comprises administering to the individual another agent to treat diabetes provided that the other agent is not insulin. In some embodiments, the method further comprises administering to the individual an agent to treat cardiovascular disease.

BRIEF DESCRIPTION OF THE FIGURES

FIG. 2A shows blood glucose (left) and body weight (right) of db/db mice after a single i.p. injection (arrow) of R1Mab1 or control IgG at indicated doses. Significance was observed in glucose (vs control IgG) between day 1-30 for all the groups and in weight (vs control IgG) on day 8 for all the groups, and between day 12-18 for 50 mpk group. N=6~14, $*p<0.05$, $**p<0.01$.

FIG. 2B shows blood glucose at random fed and overnight fasted mice (left) and serum insulin levels after overnight fast, and 30 minutes post i.p. injection of 1 g/kg glucose (right). N=6~14, $*p<0.05$, $**p<0.01$.

FIGS. 4A, 4A-1 and 4A-2 show mRNA expression (red: higher expression and blue: lower expression) in BAT for genes belonging to indicated KEGG pathway. The samples were collected at day 4 post single i.p. injection of 1 mpk R1MAb1 or pair-fed mice injected with control IgG.

FIG. 17B shows the amino acid sequences of FGFR1 (amino acids 161-212; SEQ ID NO: 27), the amino acid sequences of peptide #26 (SEQ ID NO: 28) and peptide #28 (SEQ ID NO: 29) along with the amino acids corresponding to peptide #26 from FGFR2 (SEQ ID NO: 30), FGFR3 (SEQ ID NO: 31) and FGFR4 (SEQ ID NO: 32) and the amino acids corresponding to peptide #28 from FGFR2 (SEQ ID NO: 33), FGFR3 (SEQ ID NO: 34) and FGFR4 (SEQ ID NO: 35). Differences between the peptide #26 and peptide #28 sequences in FGFR1 and the corresponding region of FGFR2-4 are boxed.

FIG. 17C shows ELISA results measuring His-tagged FGFR1 binding to FGF2 protein in the presence of various concentrations of R1MAb1 or control IgG. The data are expressed as % FGFR1-His binding and represent means±SEM (n=3).

FIG. 17D shows binding of iodinated FGF21 to HEK293 cells stably expressing both KLB and FGFR1c in the presence of various concentrations of non-labeled R1MAb1 or FGF21 (the reaction also contained BSA (10 mg/ml) and control IgG (350 mM) to block non-specific binding. The data are expressed as % bound FGF21 of total radio-labeled FGF21 in the reaction.

DETAILED DESCRIPTION OF EMBODIMENTS OF THE INVENTION

I. Definitions

Figures 1A, 1B:
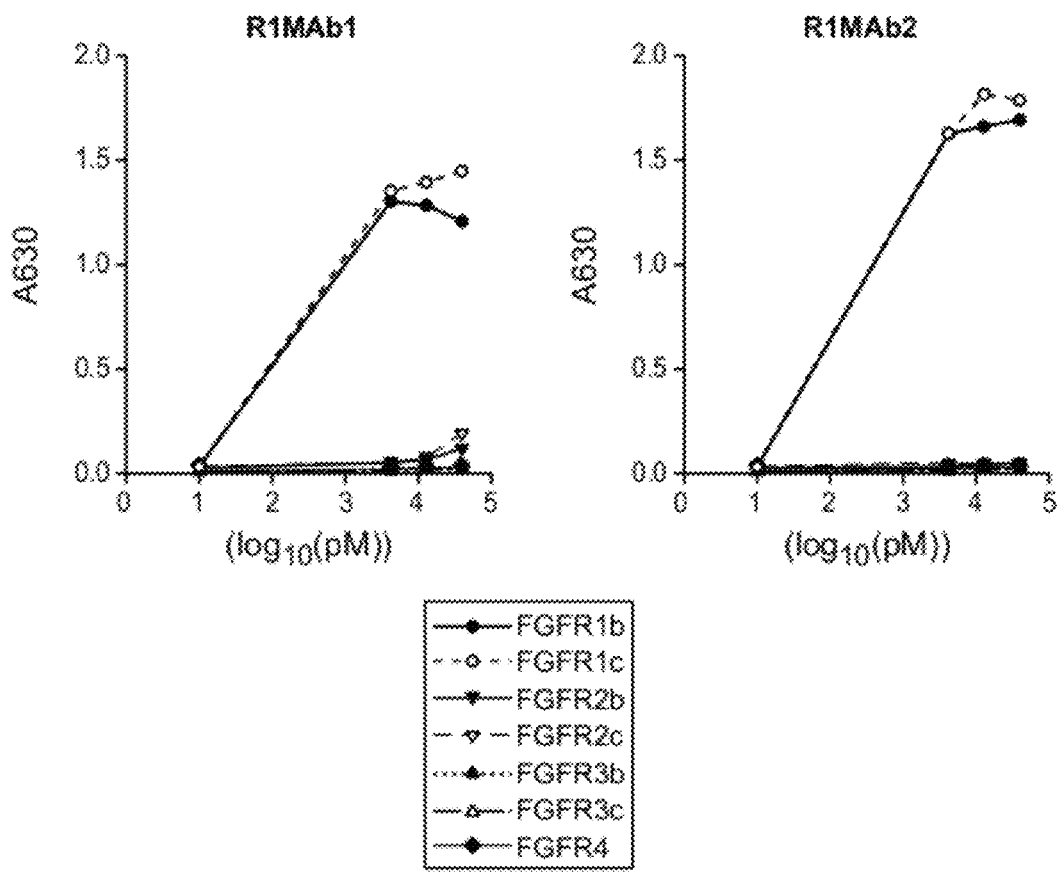
FIG. 1A shows an ELISA measuring binding of anti-FGFR1 antibodies to purified FGFR ECD fragments.
FIG. 1B shows surface plasmon resonance binding constants for R1MAb1 and R1MAb2.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "anti-FGFR1 agonist antibody" refers to an antibody that is capable of binding FGFR1 with sufficient affinity such that the antibody is useful as a therapeutic agent in activating FGFR1. In one embodiment, the extent of binding of an anti-FGFR1 antibody to an unrelated, non-FGFR1 protein is less than about 10% of the binding of the antibody to FGFR1 as measured, e.g., by a radioimmunoassay (RIA). In certain embodiments, an antibody that binds to FGFR1 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA₂. The heavy chain constant domains that correspond to the different classes of immunoglobulins are called α, δ, ε, γ, and μ, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-FGFR1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfidebonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software.

Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "Fibroblast Growth Factor Receptor 1 or FGFR1," as used herein, refers to any native FGFR1 from any vertebrate source, including mammals such as primates (e.g. humans) and rodents (e.g., mice and rats), unless otherwise indicated. The term encompasses "full-length," unprocessed FGFR1 as well as any form of FGFR1 that results from processing in the cell. The term also encompasses naturally occurring variants of FGFR1, e.g., splice variants or allelic variants. The amino acid sequence of exemplary human FGFR1b and FGFR2b, respectively, are shown below:

```
                                              (SEQ ID NO: 1)
     NTKPNPVAPYWTSPEKMEKKLHAVPAAKTVKFKCPSSGTPNPTLR

WLKNGKEFKPDHRIGGYKVRYATWSIIMDSVVPSDKGNYTCIVENEYGSI

NHTYQLDVVERSPHRPILQAGLPANKTVALGSNVEFMCKVYSDPQPHIQW
```

-continued

```
LKHIEVNGSKIGPDNLPYVQILKHSGINSSDAEVLTLFNVTEAQSGEYVC

KVSNYIGEANQSAWLTVTRPVAKALEERPAVMTS;
and
                                            (SEQ ID NO: 5)
     NTKPNPVAPYWTSPEKMEKKLHAVPAAKTVKFKCPSSGTPNPTLR

WLKNGKEFKPDHRIGGYKVRYATWSIIMDSVVPSDKGNYTCIVENEYGSI

NHTYQLDVVERSPHRPILQAGLPANKTVALGSNVEFMCKVYSDPQPHIQW

LKHIEVNGSKIGPDNLPYVQILKTAGVNTTDKEMEVLHLRNVSFEDAGEY

TCLAGNSIGLSHHSAWLTVLEALEERPAVMTS.
```

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on the discovery of anti-FGFR1 agonistic antibodies and the therapeutic activity of such antibodies. Antibodies of the invention are useful, e.g., for the treatment of metabolic diseases, including diabetes.

A. Exemplary Anti-FGFR1 Antibodies

In one aspect, the invention provides isolated antibodies that bind to FGFR1. In certain embodiments, an anti-FGFR1 antibody binds to FGFR1b and/or FGFR1c and agonizes FGFR1 activity.

In one aspect, the invention provides an anti-FGFR1 antibody comprising at least one, two, three, four, five, or six HVRs selected from (a) HVR-H1 comprising the amino acid sequence of SEQ ID NO: 26; (b) HVR-H2 comprising the amino acid sequence of SEQ ID NO: 25; (c) HVR-H3 comprising the amino acid sequence of SEQ ID NO: 17, SEQ ID NO: 18 or SEQ ID NO: 20; (d) HVR-L1 comprising the amino acid sequence of SEQ ID NO: 21; (e) HVR-L2 comprising the amino acid sequence of SEQ ID NO: 22; and (f) HVR-L3 comprising the amino acid sequence of SEQ ID NO: 23.

In some embodiments, an anti-FGFR1 antibody may be fully human, humanized or non-human. In one embodiment, an anti-FGFR1 antibody comprises HVRs as in any of the above embodiments, and further comprises an acceptor human framework, e.g. a human immunoglobulin framework or a human consensus framework.

In another aspect, an anti-FGFR1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 2, 3 or 4 as follows:

```
                                            (SEQ ID NO: 2)
EVQLVESGGGLVQPGGSLRLSCAASGFTFTSTWISWVPGKGLEWVGEIDP

YDGDTYYADSVKGRFTISADTSKNLQMNSLRAEDTAVYYCASSGYGGSDY

AMDYWGQ,
                                            (SEQ ID NO: 3)
EVQLVESGGGLVQPGGSLRLSCAASGFTFSNNYIHWVPGKGLEWVADIYP

NDGDTDYADSVKGRFTISADTSKNLQMNSLRAEDTAVYYCAREHFDAWVH

YYVMDYWGQ,
and
                                            (SEQ ID NO: 4)
EVQLVESGGGLVQPGGSLRLSCAASGFTFTSNWISWVPGKGLEWVAEIDP

YDGATDYADSVKGRFTISADTSKNLQMNSLRAEDTAVYYCATGTDVMDYW

GQ.
```

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR1 antibody comprising that sequence retains the ability to bind to FGFR1 and to agonize its activity. In certain embodiments, a total of 1 to 10 amino acids have been substituted, inserted and/or deleted in SEQ ID NO: 2, 3 or 4. In certain embodiments, substitutions, insertions, or deletions occur in regions outside the HVRs (i.e., in the FRs). Optionally, the anti-FGFR1 antibody comprises the VH sequence in SEQ ID NO: 2, 3 or 4, including post-translational modifications of that sequence.

In another aspect, an anti-FGFR1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 6 as follows:

```
                                            (SEQ ID NO: 6)
DIQMTQSPSSLSASVGDRVTITCRASQDVSTAVAWYQQKPGKAPKLLIYS

ASFLYSGVPSRFSGSGSGTDFTLTISSLQPEDFATYYCQQSYTTPPTFGQ

GTKVEIKR.
```

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-FGFR1 antibody comprising that sequence retains the ability to bind to FGFR1. In certain embodiments, a total of 1 to 10 amino acids have been substituted, inserted and/or deleted in SEQ ID NO: 6. In certain embodiments, the substitutions, insertions, or deletions occur in regions outside the HVRs (i.e., in the FRs). Optionally, the anti-FGFR1 antibody comprises the VL sequence in SEQ ID NO: 6, including post-translational modifications of that sequence.

In another aspect, an anti-FGFR1 antibody is provided, wherein the antibody comprises a VH as in any of the embodiments provided above, and a VL as in any of the embodiments provided above. In one embodiment, the antibody comprises the VH and VL sequences in SEQ ID NO: 2, 3 or 4 and SEQ ID NO: 6, respectively, including post-translational modifications of those sequences.

In a further aspect of the invention, an anti-FGFR1 antibody according to any of the above embodiments is a monoclonal antibody, including a chimeric, humanized or human antibody. In one embodiment, an anti-FGFR1 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-FGFR1 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for FGFR1 and the other is for any other antigen, e.g. beta-Klotho. In certain embodiments, bispecific antibodies may bind to two different epitopes of FGFR1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g., Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to FGFR1 as well as another, different antigen, e.g. klothoBeta (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-FGFR1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-FGFR1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-FGFR1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-FGFR1 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

2. Activity Assays

In one aspect, assays are provided for identifying anti-FGFR1 antibodies thereof having agonistic activity. For example, biological activity may include the ability to activate signal transduction of particular pathways which can be measured, e.g., by determining levels of phospho-FRS2a, phospho-MEK, phospho-ERK/MAPK, phospho-STAT3 or using the GAL-Elk1-based luciferase assays described herein (see also, e.g., Wu et al. *J. Biol. Chem.* 5; 282(40):29069-72 (2007) and Wu et al. *PLoS One* 18; 6(3):e17868 (2011)). Antibodies having such biological activity in vivo and/or in vitro are also provided.

D. Immunoconjugates

The invention also provides immunoconjugates comprising an anti-FGFR1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethyl-lauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770, 701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-FGFR1 antibodies provided herein is useful for detecting the presence of FGFR1 in a biological sample. The term "detecting" as used herein encompasses quantitative or qualitative detection. In certain embodiments, a biological sample comprises a cell or tissue, such as brown adipose tissue, pancreatic tissue, liver tissue, white adipose tissue and tumor tissue.

In one embodiment, an anti-FGFR1 antibody for use in a method of diagnosis or detection is provided. In a further aspect, a method of detecting the presence of FGFR1 in a biological sample is provided. In certain embodiments, the method comprises contacting the biological sample with an anti-FGFR1 antibody as described herein under conditions permissive for binding of the anti-FGFR1 antibody to FGFR1, and detecting whether a complex is formed between the anti-FGFR1 antibody and FGFR1. Such method may be an in vitro or in vivo method. In one embodiment, an anti-FGFR1 antibody is used to select subjects eligible for therapy with an anti-FGFR1 antibody, e.g. where FGFR1 is a biomarker for selection of patients.

In certain embodiments, labeled anti-FGFR1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^3H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-FGFR1 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, it may be desirable to further provide a glp-1 analog, a synthetic amylin, a glucagon receptor antagonist (e.g. an anti-GCGR antibody), or leptin. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the agonistic anti-FGFR1 antibodies provided herein may be used in therapeutic methods.

In one aspect, an agonistic anti-FGFR1 antibody for use as a medicament is provided. In further aspects, an agonistic anti-FGFR1 antibody for use in treating a metabolic disease is provided. In certain embodiments, an agonistic anti-FGFR1 antibody for use in a method of treatment is provided. In certain embodiments, the invention provides an agonistic anti-FGFR1 antibody for use in a method of treating an individual having a metabolic disease comprising administering to the individual an effective amount of the anti-FGFR1 antibody. In one such embodiment, the method further comprises administering to the individual an effective amount of at least one additional therapeutic agent, e.g., a glp-1 analog, a synthetic amylin, a glucagon receptor antagonist (e.g. an anti-GCGR antibody), or leptin. An "individual" according to any of the above embodiments is preferably a human.

In a further aspect, the invention provides for the use of an agonistic anti-FGFR1 antibody in the manufacture or preparation of a medicament. In one embodiment, the medicament is for treatment of a metabolic disease. In a further embodiment, the medicament is for use in a method of treating metabolic disease comprising administering to an individual having the disease an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating a metabolic disease. In one embodiment, the method comprises administering to an individual having such metabolic disease an effective amount of an agonistic anti-FGFR1 antibody. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the agonistic anti-FGFR1 antibodies provided herein, e.g., for use in any of the above therapeutic methods. In one embodiment, a pharmaceutical formulation comprises any of the agonistic anti-FGFR1 antibodies provided herein and a pharmaceutically acceptable carrier. In another embodiment, a pharmaceutical formulation comprises any of the agonistic anti-FGFR1 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a glp-1 analog, a synthetic amylin, a glucagon receptor antagonist (e.g. an anti-GCGR antibody), or leptin.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

Example 1

Generation and Characterization of Anti-FGFR1 Agonist Antibodies

We generated monoclonal antibodies specific to FGFR1 using phage display technology and His-tagged IgD2-D3 of human FGFR1b and c as antigens. Human phage antibody libraries with synthetic diversities in the selected complementary determining regions (H1, H2, H3, L3), mimicking the natural diversity of human IgG repertoire were used for panning. The Fab fragments were displayed bivalently on the surface of M13 bacteriophage particles (Lee et al., *J. Immunol. Methods* 284:119-32 (2004)). The panning protocol was described previously (Liang et al., *J. Mol. Biol.* 366:815-29 (2007)). After screening many clones from multiple libraries, unique and specific phage antibodies that bind to both b and c isoforms of FGFR1 were identified by phage ELISA. To test binding of the antibodies to human FGFRs, conventional ELISA protocol was employed using 2 μg/ml of FGFR1 ECD-human Fc chimeric proteins.

We also measured binding affinities of anti-FGFR1 antibodies to FGFR1 were measured by Biacore/SPR using a BIAcore™ T100 instrument as described (Liang et al., supra) with the following modifications. Mouse anti-human Fc antibody was first coated on a BIAcore™ carboxymethylated dextran CM5 chip using direct coupling to free amino groups following a procedure described by the manufacturer. Antibody was then captured on CM5 biosensor chips to achieve approximately 200 response units (RU). Binding measurements were performed using a running buffer composed of 10 mM HEPES pH 7.4, 150 mM NaCl, 0.005% surfactant P20 (HBS-P buffer). A 2-fold dilution series of FGFR1 ECD-His protein was injected in a range of 1.550 nM in HBS P buffer at a flow rate of 30 μL/minute at 25° C. Association rates (Kon, per mol/s) and dissociation rates (Koff, per s) were calculated using a simple one-one Langmuir binding model (BIAcore™ Evaluation Software version 3.2). The equilibrium dissociation constant (Kd, per mol) was calculated as the ratio of Koff/Kon.

Figures 1, 1C:
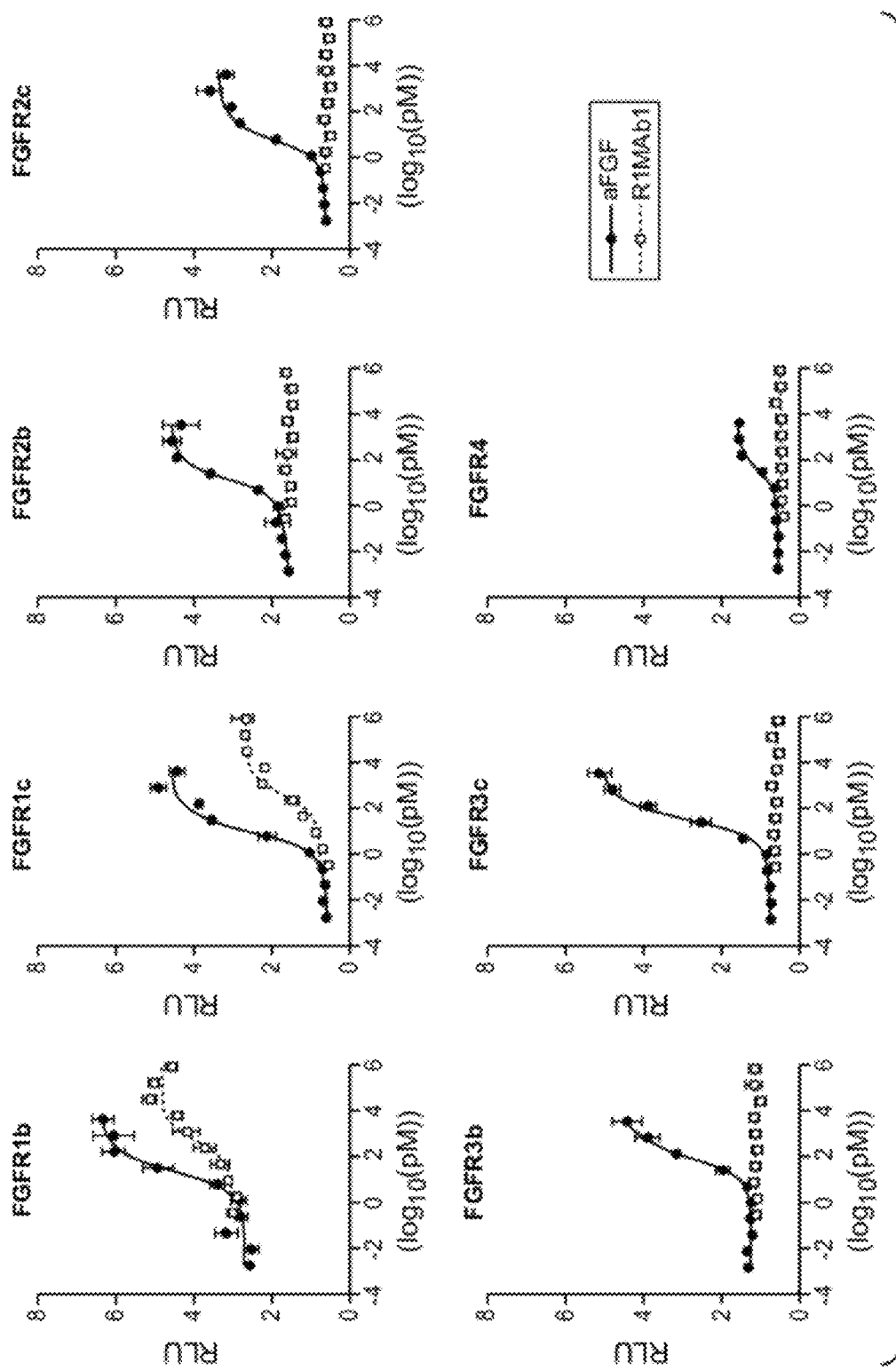
FIGS. 1C-1 and 1C-2 show a GAL-Elk1 luciferase assay in rat L6 cells. Cells were cotransfected with an expression vectors for the indicated FGFR isoform together with GAL-Elk1, SV40-renilla Luciferase, and Gal-responsive firefly luciferase reporter. Transfected cells were incubated with media containing increasing concentrations of R1Mab or acidic FGF (aFGF: positive control) for 6 hours before luciferase assays. Transcriptional activation was assessed by the relative firefly luciferase activity normalized by renilla luciferase activity and expressed as relative luciferase unit (RLU).
Figures 1, 1C, 2:
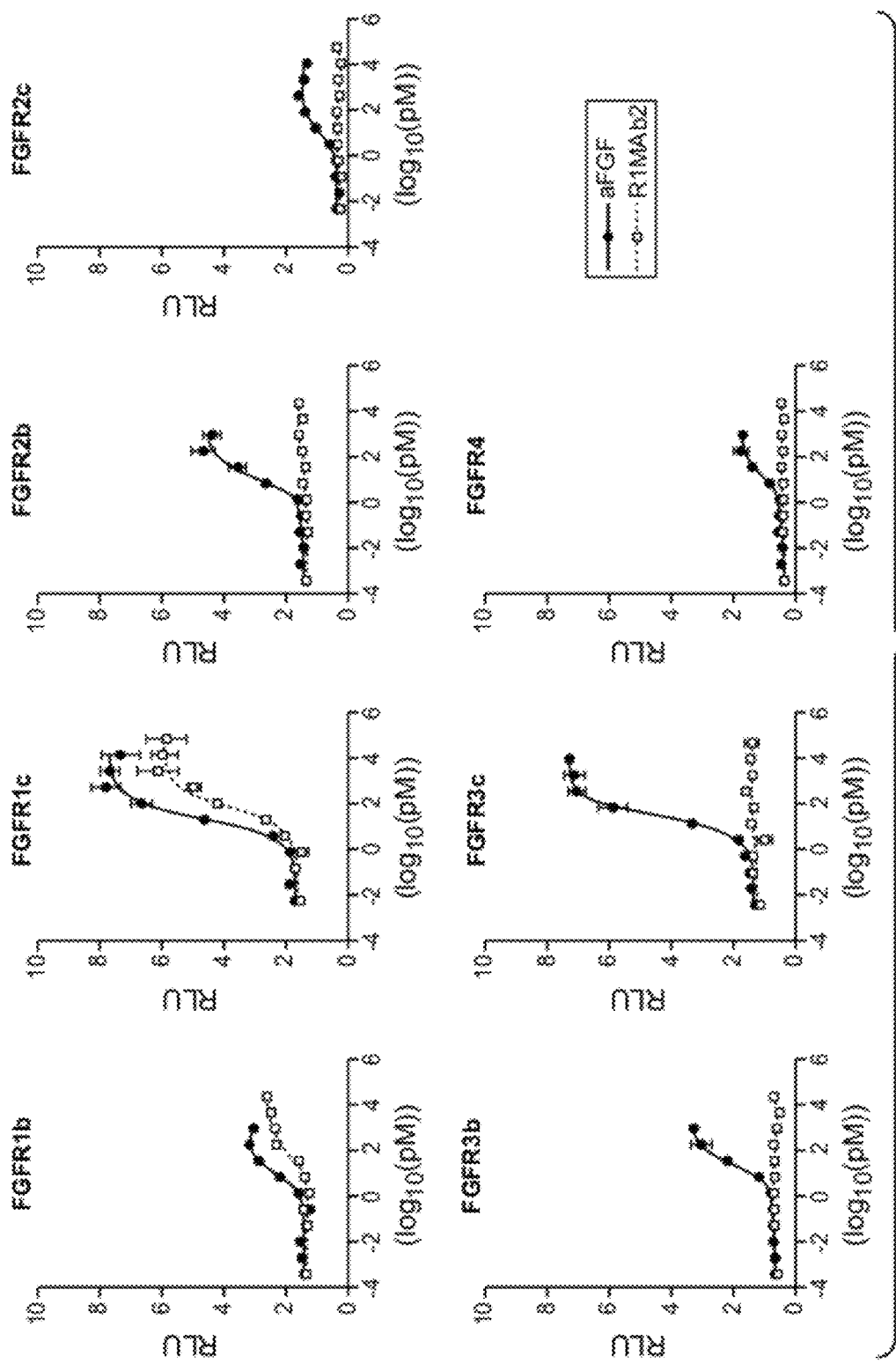
Figures 1D, 1E:
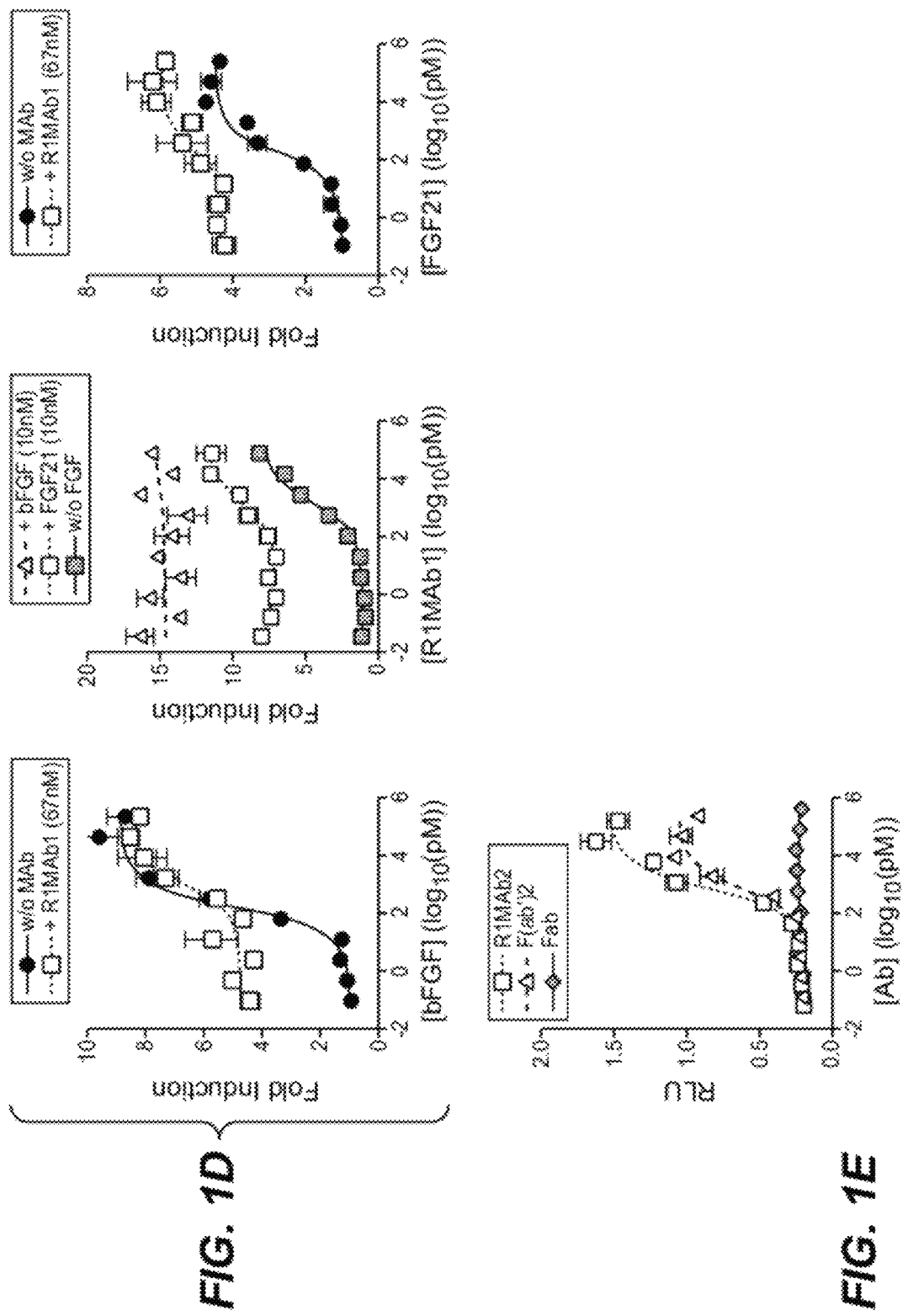
FIG. 1D shows an experiment similar to that shown in FIGS. 1C-1 and 1C-2 except L6 cells expressed both FGFR1c and KLB.
FIG. 1E shows an experiment similar to that shown in FIGS. 1C-1 and 1C-2 except HEK293 cells were used.
Figure 1F:
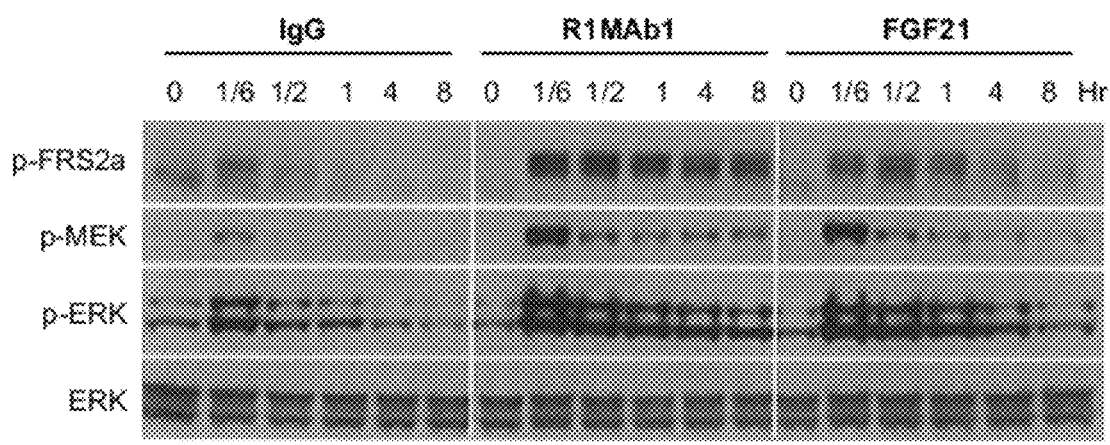
FIG. 1F shows western blot analysis of 3T3-L1 adipocytes treated with indicated protein at 0.5 μg/ml for indicated time.
Figure 1G:
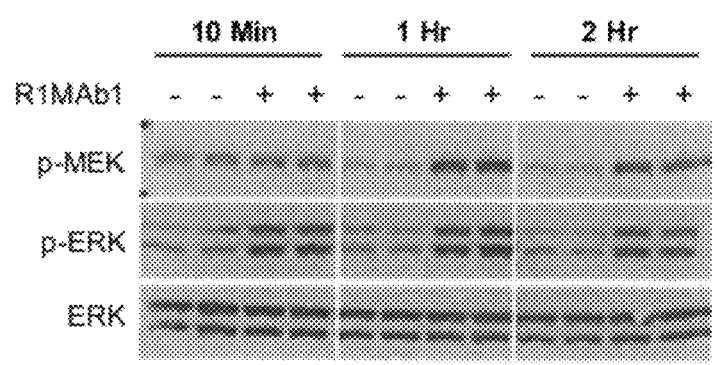
FIG. 1G shows WAT harvested from lean C57BL/6 mice at indicated time after i.p. injection at 1 mpk of R1Mab (+) or control IgG (−), and subjected to western blot analysis.
Figure 5:
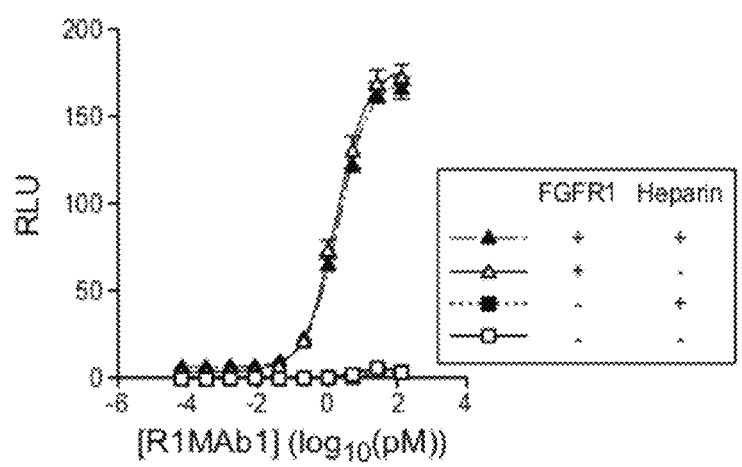
FIG. 5 shows heparin-independent and FGFR1-dependent agonistic activity of R1MAb1. GAL-Elk1 luciferase assay in HEK293 cells. Cells were cotransfected with or without an expression vectors for FGFR1c as indicated, together with GAL-Elk1, SV40-renilla Luciferase, and Gal-responsive firefly luciferase reporter. Transfected cells were incubated in media containing increasing concentrations of R1Mab1 with or without 25 mg/L porcine heparin as indicated for 6 hours before luciferase assays. Transcriptional activation was assessed by the relative firefly luciferase activity normalized by renilla luciferase activity and expressed as relative luciferase unit (RLU).
Figure 6A:
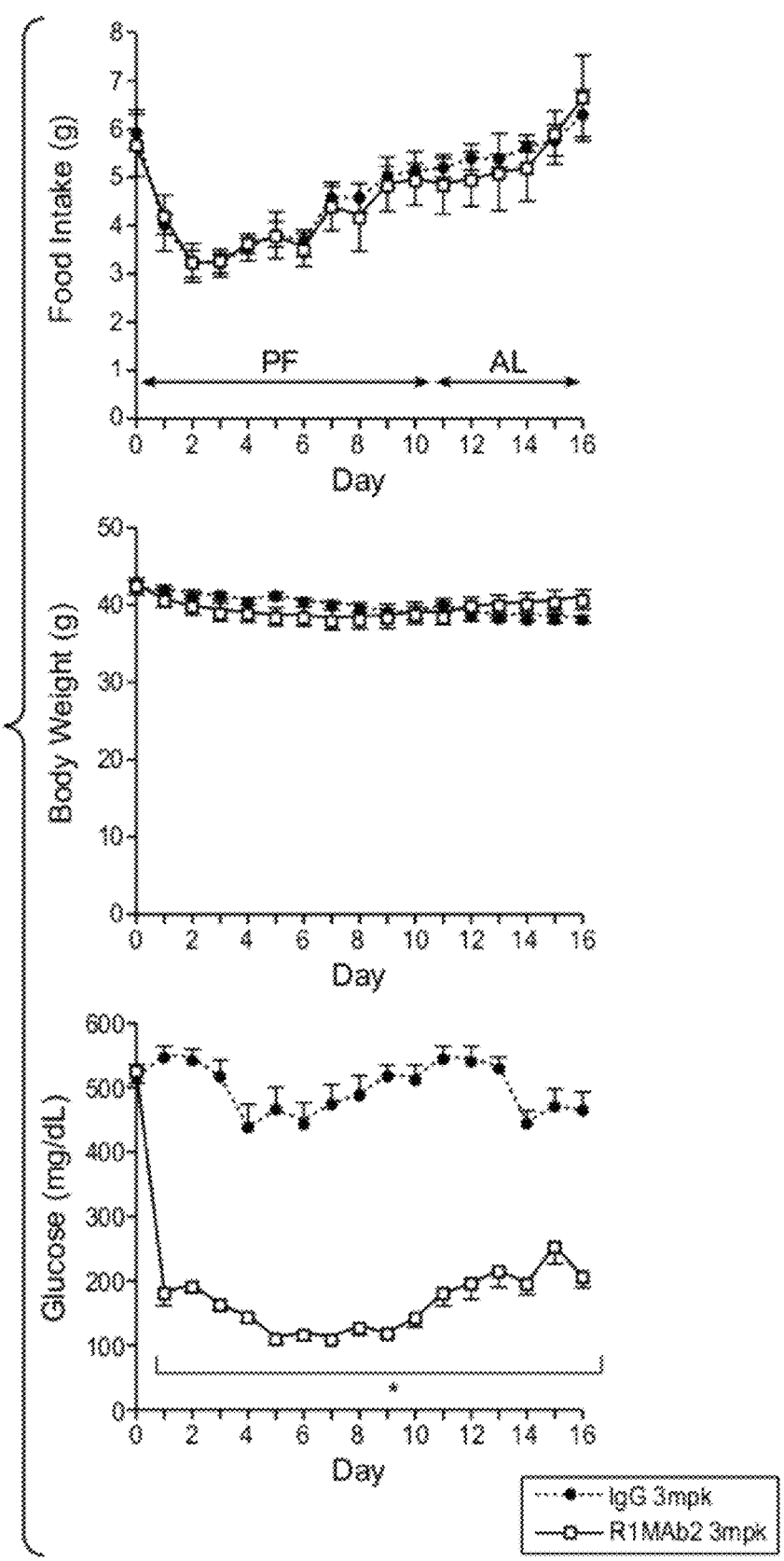
FIG. 6A shows food intake (top), body weight (center), and blood glucose (bottom) of db/db mice after a single i.p. injection of R1Mab2 or control IgG at 3 mpk doses on day 0. The control mice were pair-fed (PF) to adjust food intake until day 11. At day 11, the food intake of R1MAb2-treated mice returned to normal, and thus all the mice were fed ad libitum after day 11 (AL). N=7~12. $p<0.001$.
Figure 6B:
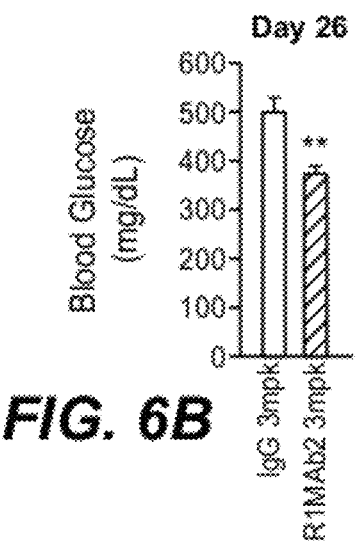
FIG. 6B shows random fed blood glucose level of mice used in FIG. 6A on day 26.
Figure 6C:
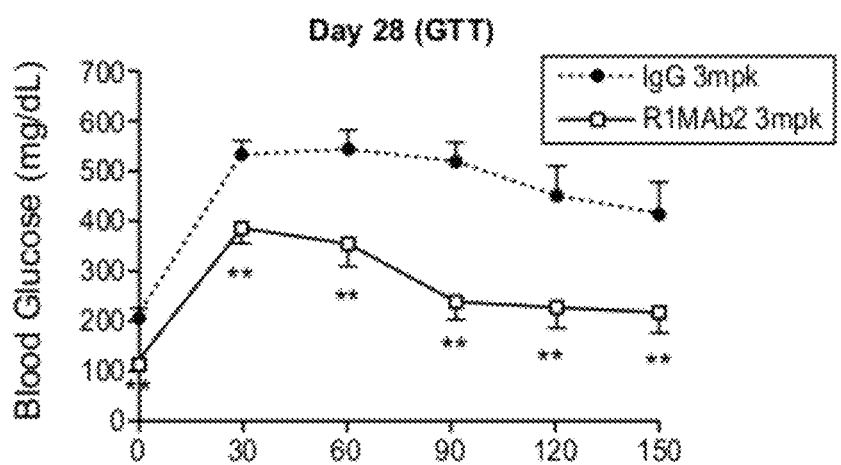
FIG. 6C shows GTT conducted using the same mice on day 28.
Figure 6D:
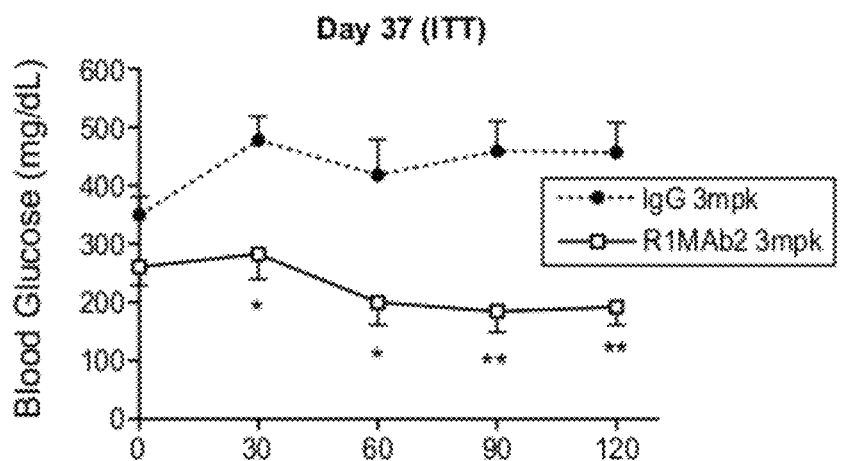
FIG. 6D shows ITT conducted using the same mice on day 37.
Figure 7A:
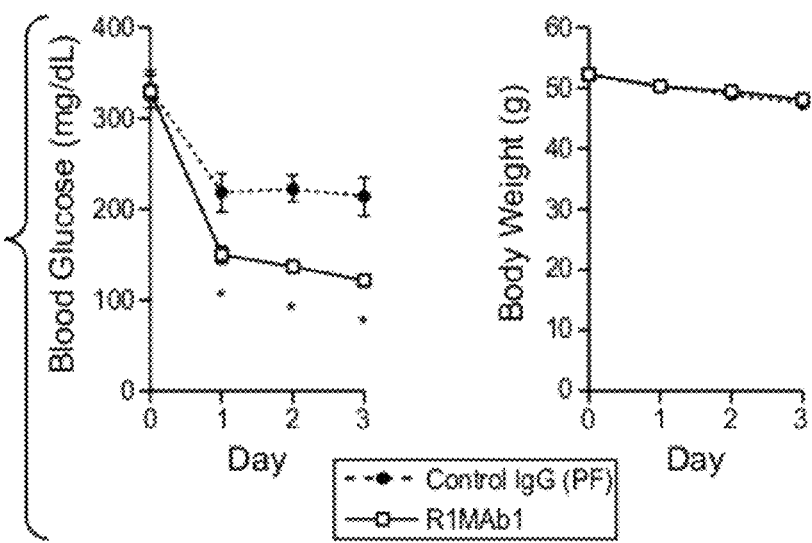
FIG. 7A shows blood glucose (left) and body weight (right) of ob/ob mice after a single i.p. injection of R1Mab1 or control IgG at 1 mpk doses on day 0. The control mice were pair-fed (PF) to R1MAb-treated group. N=7. $*p<0.05$ (vs PF-IgG).
Figure 7B:
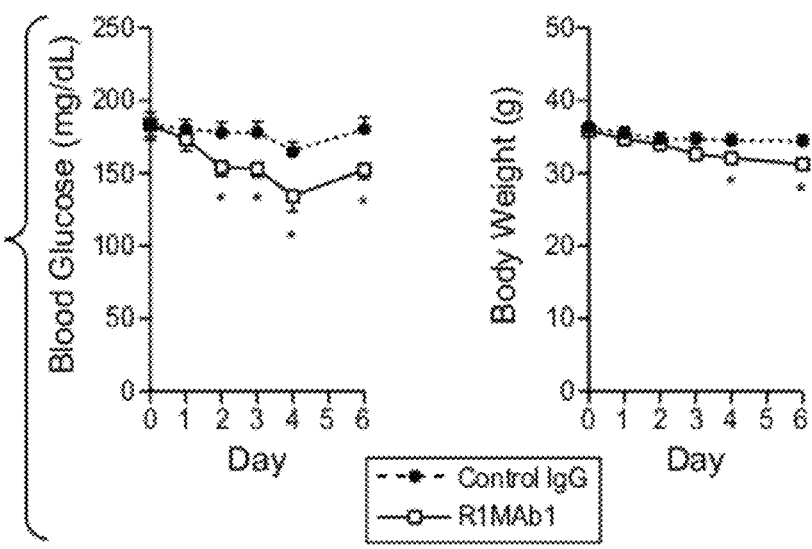
FIG. 7B shows blood glucose (left) and body weight (right) of HFD-fed C57BL/6 mice after a single i.p. injection of R1Mab1 or control IgG at 1 mpk on day 0. N=7~9. $*p<0.05$.
Figure 7C:
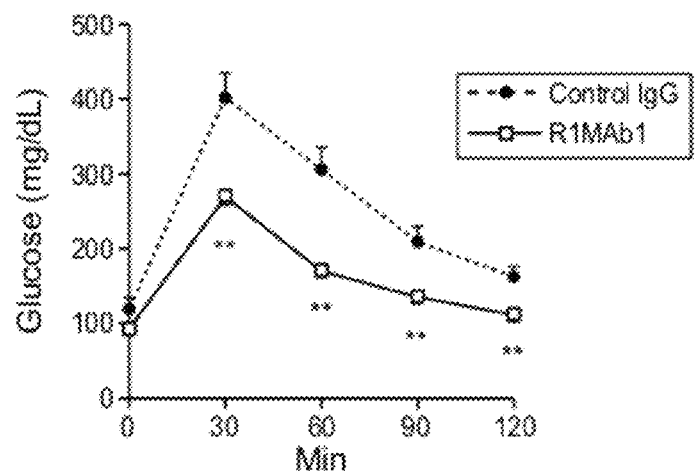
FIG. 7C shows GTT conducted HFD-fed mice used in FIG. 7B on day 8 post Ab injection. Mice were injected i.p. with 1 g/kg glucose after overnight fast. Mean body weights were 28.6+/−0.6 (R1MAb1) and 32.1+/−0.8 (control IgG) ($p<0.01$). N=7.
Figure 7D:
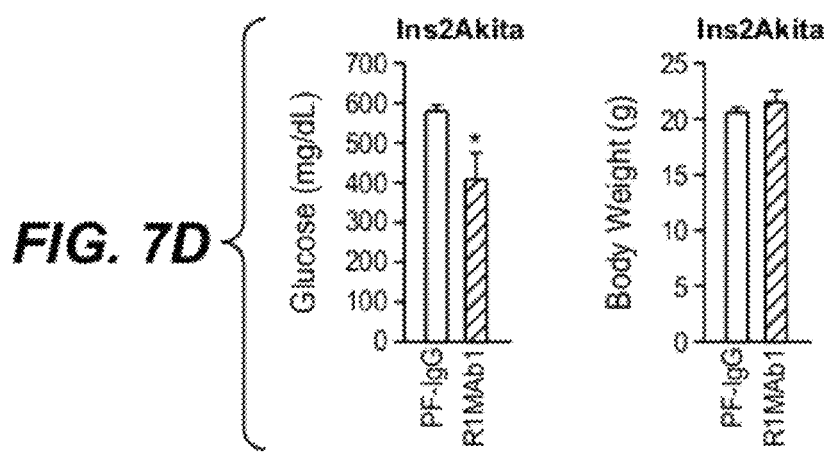
FIG. 7D shows blood glucose (left) and body weight (right) of Ins2Akita mice on day 5 post single i.p. injection of R1Mab1 or control IgG at 1 mpk. The control mice were pair-fed (PF-IgG) to normalize body weight. $* p<0.05$.

Two of the anti-FGFR1 antibodies which were identified as described above in independent experiments (designated here as R1MAb1 and R1MAb2) bind to FGFR1b and FGFR1c at a similar affinity, but not to any other FGFR isoforms (FIGS. 1A and B). Their signaling activity was tested using a Gal-Elk1 based luciferase assay in rat L6 cells lacking endogenous FGFRs, but transfected to express each FGFR isoform (and KLB as necessary). These antibodies were unexpectedly potent agonists: both R1MAbs induced luciferase activity in a dose dependent manner, but only when cells express recombinant FGFR1b or FGFR1c, indicating that R1MAbs act as specific agonist for FGFR1 (FIG. 1C). In this assay format, R1MAbs did not appreciably affect activity of basic FGF (bFGF), a classical FGFR1 ligand (FIG. 1D). However, R1MAbs and FGF21 showed an additive effect when cells express FGFR1c and KLB (FIG. 1D). F(ab')2 but not Fab fragment of R1MAb2 showed FGFR1-dependent agonistic activity, suggesting that the R1MAbs exert their agonistic activity by promoting homodimerization of FGFR1 (FIG. 1E). Previously, an artificial FGFR dimerizing agonist containing an FGFR1-binding peptide and the c-jun leucine zipper domain had been reported. This molecule called C19jun also binds to heparin through the c-jun domain and requires heparin for FGFR1 activation (Ballinger et al., *Nature Biotechnol.* 17: 1199-1204 (1999)). In contrast, heparin did not affect agonistic activity of R1MAb1 in the luciferase assay (FIG. 5). Heparin-independent agonistic activity of the R1MAb1 was further confirmed by examining phosphorylation of ERK and MEK1/2, signaling components downstream of FGFRs, in cultured murine 3T3-L1 adipocytes (FIG. 1F) or in WAT of C57BL/6 mice injected intraperitoneally with R1MAb (FIG. 1G).

Figure 17A:
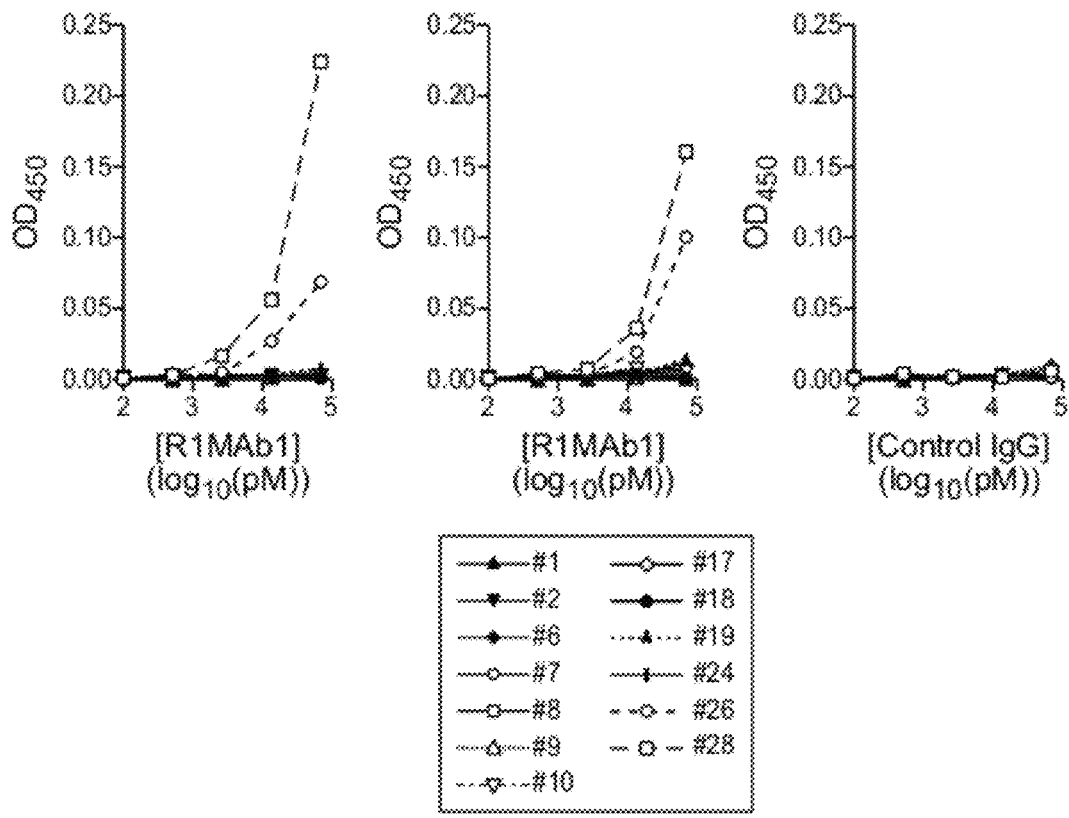
FIG. 17A shows ELISA results measuring antibody binding to biotinylated peptide fragments.

We performed experiments to map the FGFR1 epitope bound by R1MAb1 and R1MAb2. We synthesized 30 peptides represented portions of the FGFR1 sequence with an amino-terminal biotin tag and used them for ELISA binding assays. These sequences of the peptides were as follows: #1: SSSEEKETDNTKPNPVAPY (SEQ ID NO: 36); #2: PVAPYWTSPEKMEKKLHAV (SEQ ID NO: 37); #3: KLHAVPAAKTVKFKCPSSG (SEQ ID NO: 38); #4: CPSSGTPNPTLRWLKNGKE (SEQ ID NO: 39); #5: KNGKEFKPDHRIGGYKVRY (SEQ ID NO: 40); #6: YKVRYATWSIIMDSVVPSD (SEQ ID NO: 41); #7: VVPSDKGNYTCIVENEYGS (SEQ ID NO: 42); #8: NEYGSINHTYQLDVVERSP (SEQ ID NO: 43); #9: VERSPHRPILQAGLPANKT (SEQ ID NO: 44); #10: PANKTVALGSNVEFMCKVY (SEQ ID NO: 45); #11: MCKVYSDPQPHIQWLKHIE (SEQ ID NO: 46); #12: LKHIEVNGSKIGPDNLPYV (SEQ ID NO: 47); #13: NLPYVQILKTAGVNTTDKE (SEQ ID NO: 48); #14: TTDKEMEVLHLRNVSFEDA (SEQ ID NO: 49); #15: SFEDAGEYTCLAGNSIGLS (SEQ ID NO: 50); #16: SIGLSHHSAWLTVLEALEE (SEQ ID NO: 51); #17: YWTSPEKMEKKLHAVPAAK (SEQ ID NO: 52); #18: EKMEKKLHAVPAAKTVKFK (SEQ ID NO: 53); #19: PAAKTVKFKCPSSGTPNPT (SEQ ID NO: 54); #20: KFKCPSSGTPNPTLRWLKN (SEQ ID NO: 55); #21: GTPNPTLRWLKNGKEFKPD (SEQ ID NO: 56); #22: TLRWLKNGKEFKPDHRIGG (SEQ ID NO: 57); #23: FKPDHRIGGYKVRYATWSI (SEQ ID NO: 58); #24: HRIGGYKVRYATWSIIMDS (SEQ ID NO: 59); #25: LHAVPAAKTVKFKCPSS (SEQ ID NO: 60); #26: KLHAVPAAKTVKFKCP (SEQ ID NO: 28); #27: AVPAAKTVKFKCPSSG (SEQ ID NO: 61); #28: FKPDHRIGGYKVRY (SEQ ID NO: 29); #29: KPDHRIGGYKVR (SEQ ID NO: 62); #30: GTPNPTLRWLKN (SEQ ID NO: 63). As shown in FIG. 17A, for both R1MAb1 and R1MAb2 the shortest peptides to which they demonstrated significant binding were peptides #26 and #28.

Example 2

R1MAbs Demonstrate Sustained Anti-Diabetic Activity

Figure 3A:
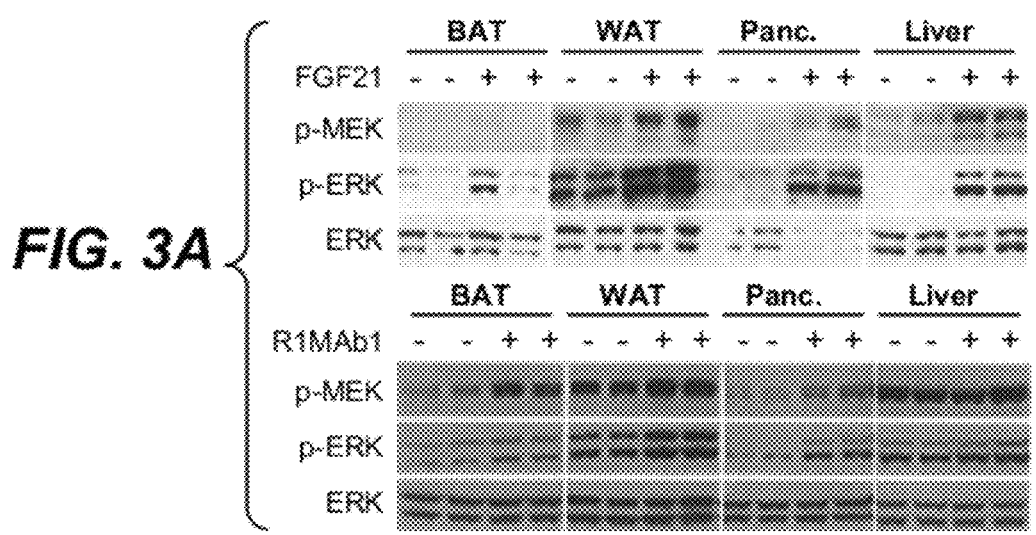
FIG. 3A shows MAPK signaling activation in mouse tissues. Indicated tissues were harvested at 15 minutes (25 μg/mouse FGF21: top) or 1 hour (1 mpk R1Mab1: bottom) after i.p. injection of lean C57BL/6 mice and subjected to Western blot analysis. PBS (top) and control IgG (bottom) were used as a negative control.
Figure 3B:
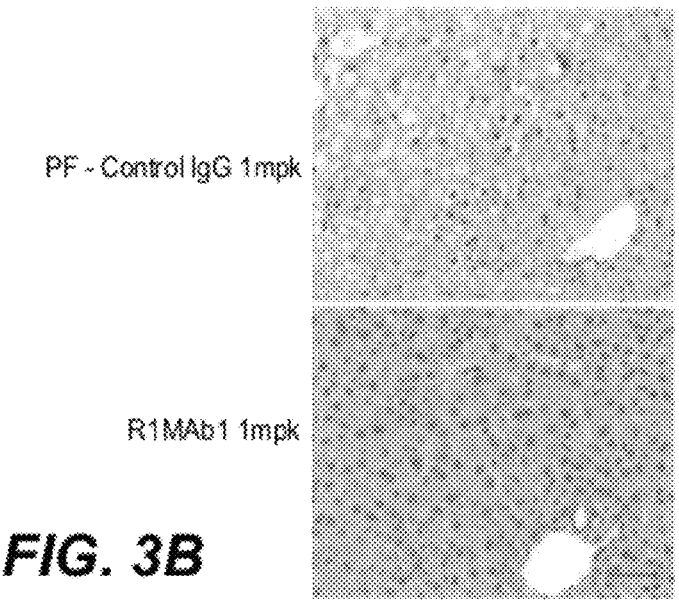
FIGS. 3B-D shows representative H&E staining of liver (B), hepatic lipids (C), and serum lipids (D). The samples were collected at day 7 post single i.p. injection of 1 mpk R1MAb1. Control mice were pair-fed to normalize body weight. N=7, $*p<0.05$, $**p<0.001$.
Figure 3C:
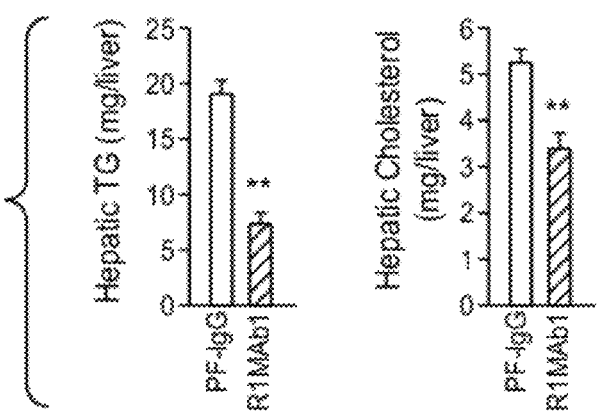
Figure 3D:
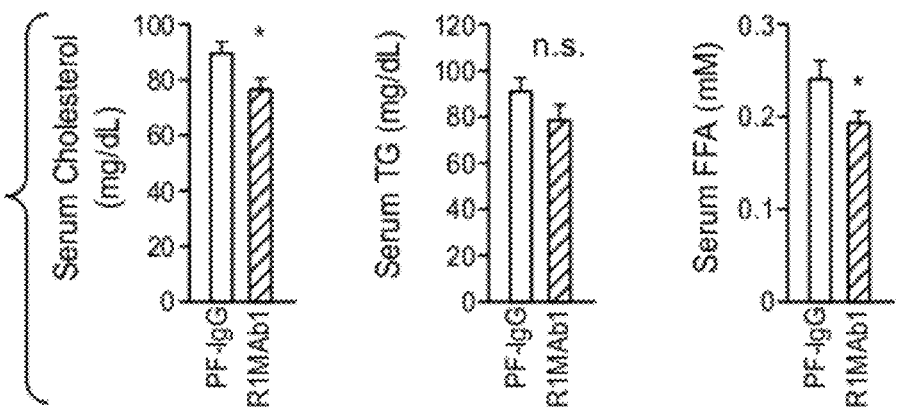
Figure 3E:
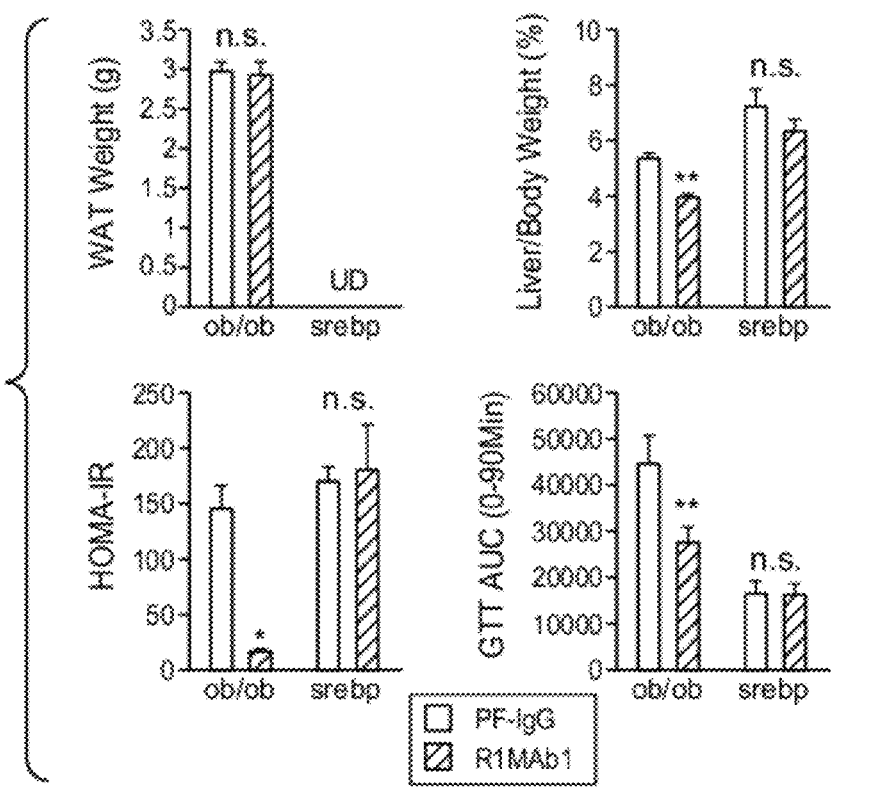
FIG. 3E shows metabolic parameters of ob/ob or transgenic ap2-SREBP1c (srebp) mice injected with 1 mpk Ab. Control groups were pair-fed to normalize body weight (FIG. 11). Glucose and Insulin for HOMA-IR calculation was measured on day 3 after 3 hour fast. GTT was conducted with 1 g/kg i.p. glucose injection on day 4 after overnight fast. Tissue weight was measured on day 5. N=7, $*p<0.05$, $***p<0.01$
Figure 3F:
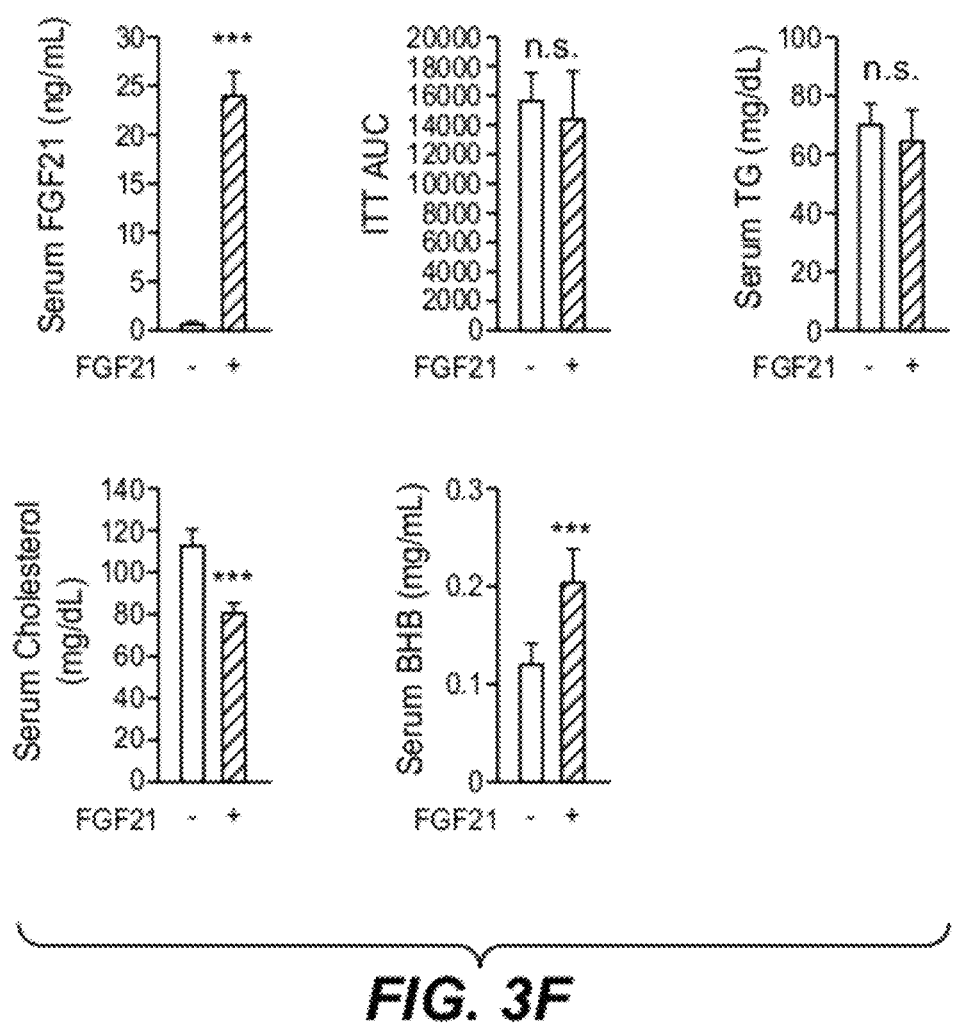
FIG. 3F shows metabolic parameters of ap2-SREBP mice subcutaneously implanted with an osmotic pump to infuse FGF21 (12 ng/day). ITT with 1 U/kg insulin i.p. injection was conducted on day 4. Serum was collected on day 6. N=6~8.

We tested whether the anti-FGFR1 antibodies of the invention would have anti-diabetic activity using mouse models of diabetes. All the mice were purchased from Jackson Laboratory and maintained in a pathogen-free animal facility at 21° C. under standard 12 hr light/12 hr dark cycle with access to chow (a standard rodent chow (Labdiet 5010, 12.7% calories from fat) or a high fat, high carbohydrate diet (Harlan Teklad TD.03584, 58.4% calories from fat) and water ad libitum. db/db mice in C57BLKS/J background were females and other mice were all males. All the mice were used for injection around 9-11 weeks old, except ap2-SREBP1c mice were 8 months old (FIG. 3E) or 4 months old (FIG. 3F). For continuous infusion of FGF21 protein, an osmotic pump (Alzet® 2001) was subcutaneously implanted. Glucose levels were measured using OneTouch® Ultra® glucometer. For hepatic lipid analysis, the lipid was extracted according to the Folch method and resuspended in PBS containing 5% Triton X-100. Total cholesterol, triglyceride, β-hydroxybutylate (Thermo DMA) and nonesterified fatty acid (Roche) were determined by using enzymatic reactions. Serum insulin levels were determined by ELISA (Crystal Chem).

Figure 2C:
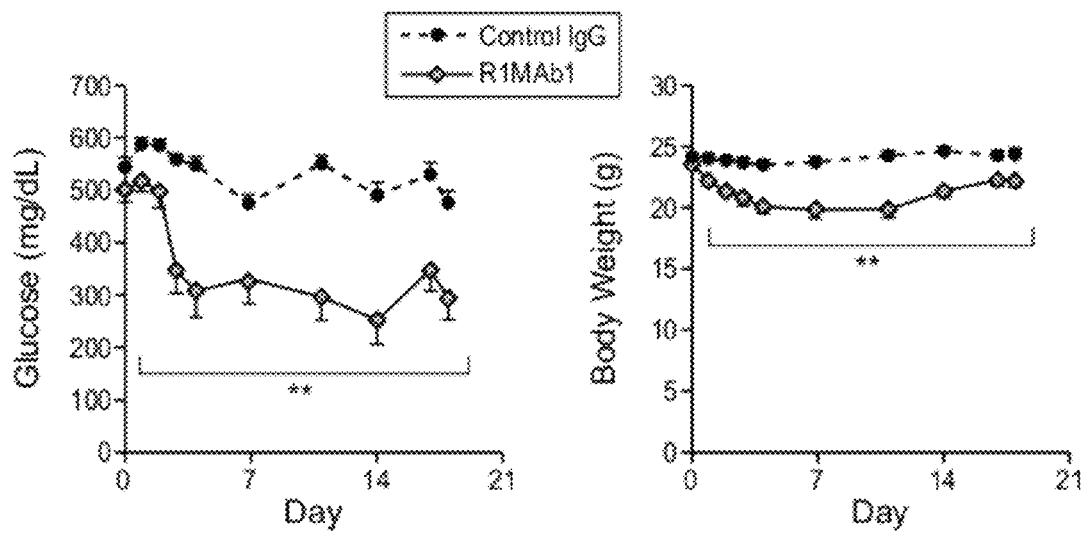
FIG. 2C shows blood glucose (left) and body weight (right) of Ins2Akita mice after a single i.p. injection of R1Mab1 or control IgG at 3 mpk. N=10. $*p<0.01$.
Figure 2D:
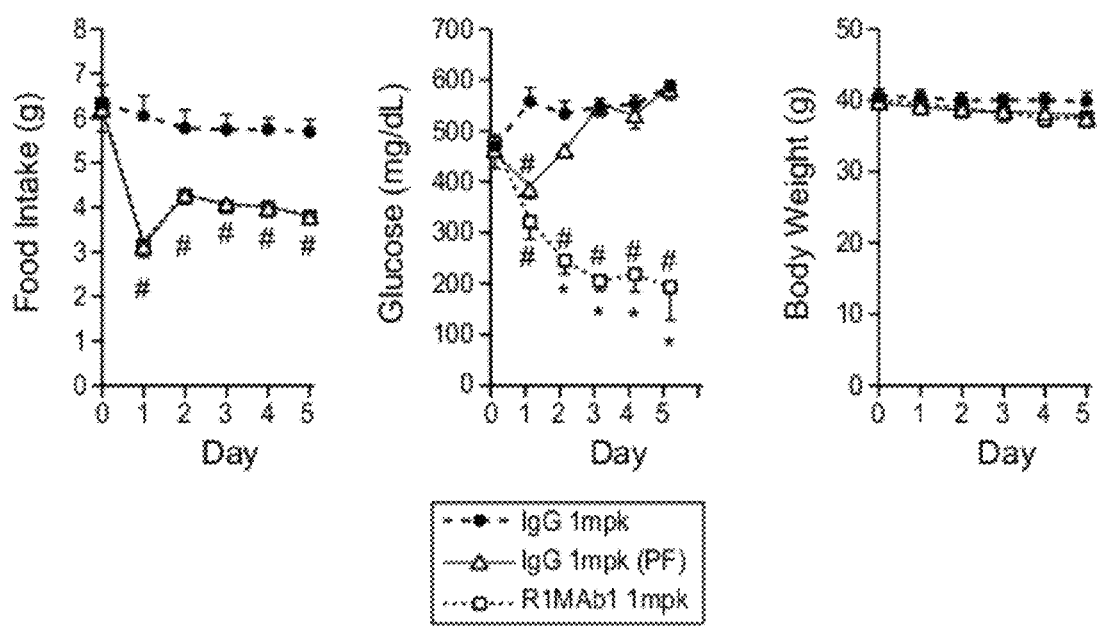
FIG. 2D shows food intake (left), blood glucose (center), and body weight (right) of db/db mice after a single i.p. injection of R1Mab1 or control IgG at 1 mpk doses. PF: pair-fed to R1MAb-treated group. N=7. $\#p<0.001$ (vs IgG), $*p<0.001$ (vs PF-IgG).
Figure 2E:
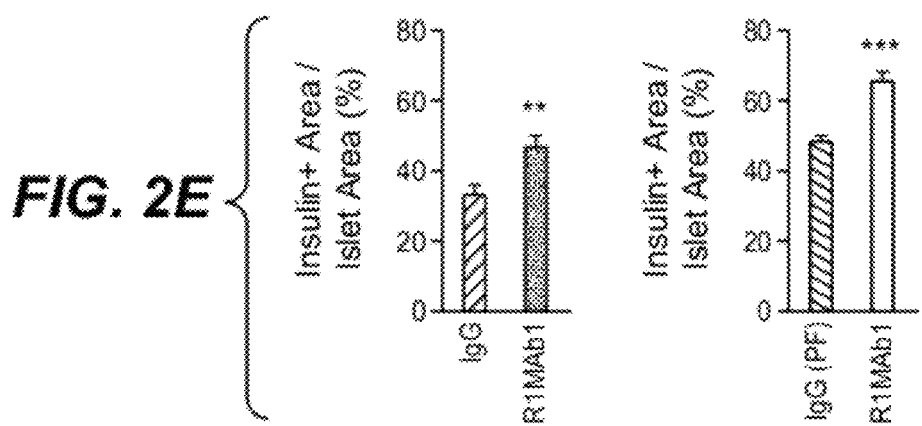
FIG. 2E shows quantification of insulin positive area in fixed pancreatic sections. The tissues were collected at day 7 post single i.p. injection of 3 mpk (left) or 1 mpk (right) R1MAb1 and stained for insulin and glucagon. N=4~7. $p<0.002$. $*p<0.001$.
Figure 8A:
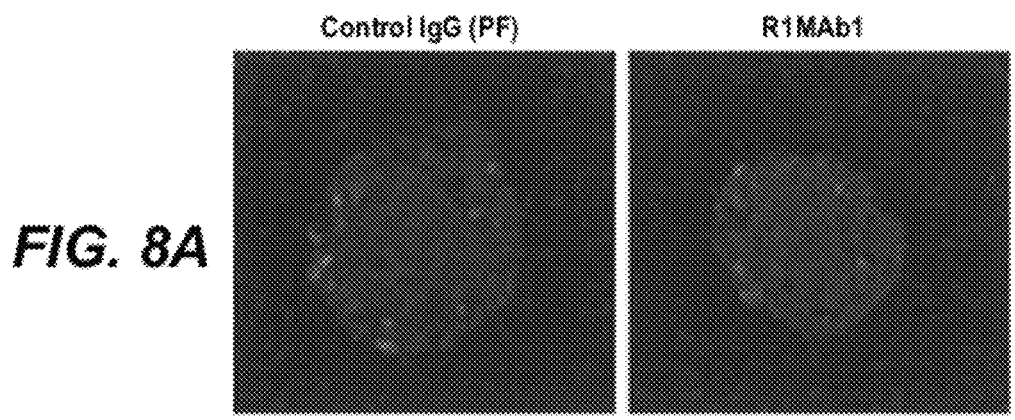
FIG. 8A shows the representative staining of pancreatic islet in db/db mice analyzed in FIG. 4E. Red: Insulin, Green: Glucagon, Blue: Nuclei. Note that R1MAb did not affect the overall morphology of islets.
Figure 8B:
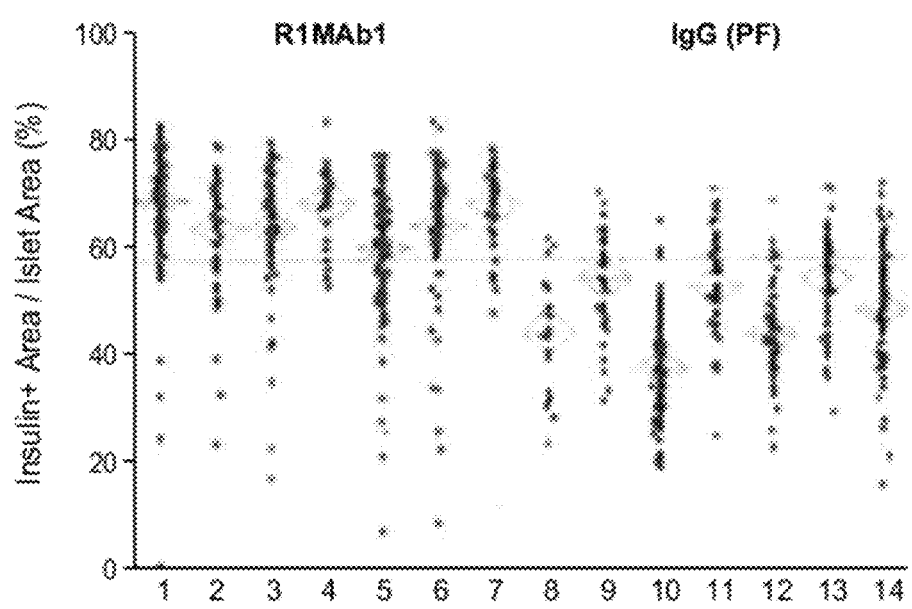
FIG. 8B shows the distribution of insulin positive area (%) in each islet in each animal.

We tested the agonistic activity of the R1MAbs in vitro and in vivo, by injecting hyperglycemic Leptin-resistant db/db mice with 3, 10, and 50 mg/kg (mpk) of R1MAb1. We observed that blood glucose levels were normalized for over a week at all three doses, and the observed glucose-lowering effect was unexpectedly strong and long-lasting, with glucose levels staying lower than the control mice for over 30 days after a single injection (FIG. 2A). This was associated with a transient, but significant decrease in body weight (FIG. 2A). The glucose lowering effect was likely through an improvement in insulin sensitivity, as serum insulin level was also dramatically decreased by R1MAb1 injection (FIG. 2B). We observed a similar R1MAb-induced reduction in blood glucose levels with R1MAb2 (FIG. 6), and in three additional mouse models with marked insulin resistance, Leptin-deficient ob/ob mice, high-fat diet (HFD) fed mice, and Ins2Akita mice (Hong et al., *Am. J. Physiol. Endocrinol. Metab.* 293: E1687-96 (2007)) (FIGS. 2C and 7). Pair-feeding experiments showed that R1MAb-induced weight loss in db/db and Ins2Akita mice is due to a reduction in food intake; however, the observed reduction in blood glucose is largely independent of food intake (FIGS. 2D and 6-7). In the pancreas, R1MAb1 injection increased insulin positive area per each islet compared with either pair-fed or non-paired control mice (FIGS. 2E and 8). FGFR1 is expressed in pancreatic β cells (Hart et al., *Nature* 408:864-68 (2000)) and FGF21 promotes β cell function ex vivo (Wente et al., *Diabetes* 55:2470-78 (2006)); thus activation of FGFR1 in β cells could directly contribute to the increased pancreatic insulin levels. These data demonstrate that activation of FGFR1 (but not FGFR2 or FGFR3) is sufficient to recapitulate anti-diabetic and anti-lipidemic activities of recombinant FGF21.

Figure 9A:
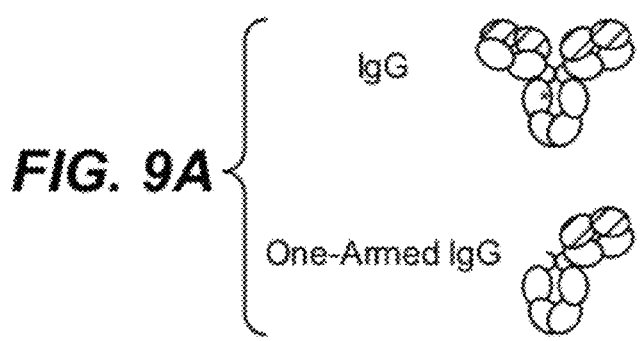
FIG. 9A shows a schematic representation of IgG and the One-Armed (OA) IgG. Blue: Heavy chain, Green: Light Chain. Red asterisk indicates approximate position of the residues mutated in the DANA mutant.
Figure 9B:
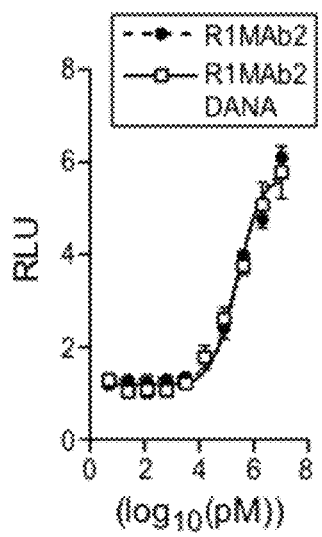
FIG. 9B shows a GAL-Elk based luciferase assay in HEK293 cells expressing FGFR1c to compare R1MAb2 and the DNA mutant of R1MAb2 (R1MAb2 DANA).
Figure 9C:
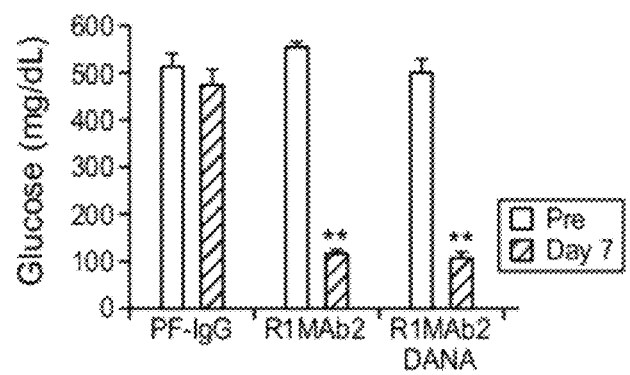
FIG. 9C shows blood glucose of db/db mice before (pre) and day 7 post i.p. injection of indicated Ab at 1 mpk. The control mice were pair-fed to normalize body weight.
Figure 9D:
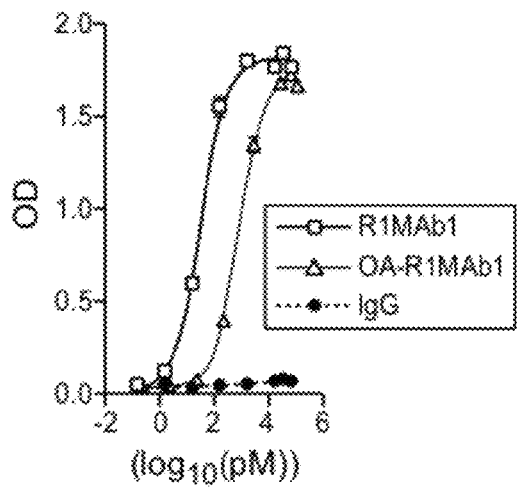
FIG. 9D shows an ELISA measuring antibody binding to purified FGFR ECD fragments. OA-R1MAb1: OA-version of R1MAb1.
Figure 9E:
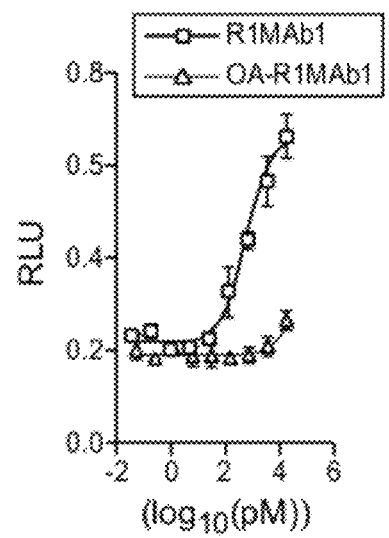
FIG. 9E shows a GAL-Elk based luciferase assay similar to FIG. 9B.
Figure 9F:
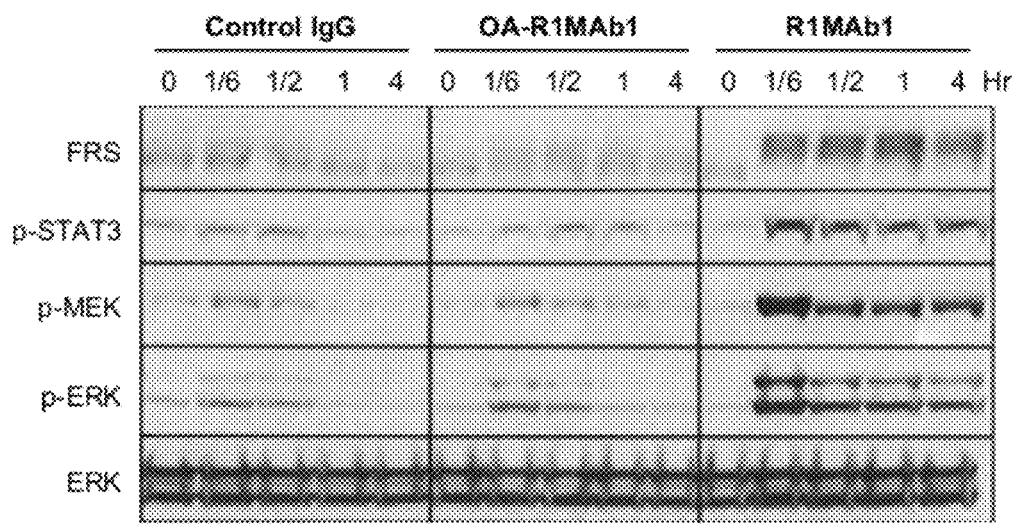
FIG. 9F shows western blot analysis of 3T3-L1 adipocytes treated with indicated protein at 0.5 µg/ml for indicated time.
Figure 9G:
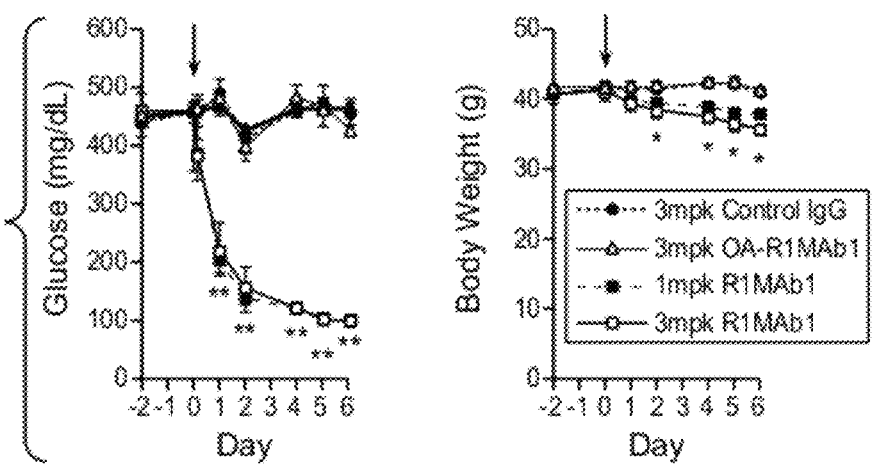
FIG. 9G shows blood glucose (left) and body weight (right) of db/db mice after a single i.p. injection of indicated Ab on day 0 (arrow). N=7. $*p<0.05$ (control IgG vs 3 mpk R1MAb1), $**p<0.0005$ (control IgG vs 3 mpk R1MAb1 and control IgG vs 1 mpk R1MAb1).
Figure 9H:
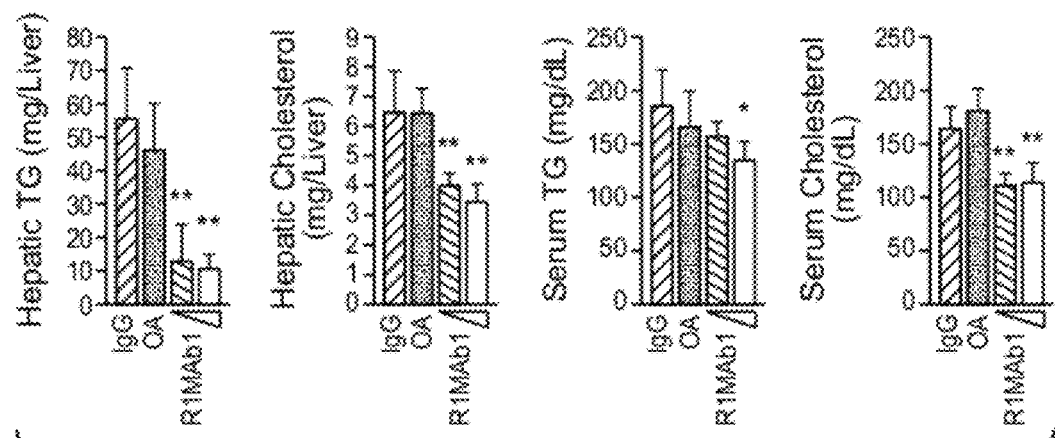
FIG. 9H shows hepatic and serum lipids from samples were collected on day 7 post Ab injection. N=7. $*p<0.05$, $**p<0.0005$ (vs control IgG).

To dissect the importance of the IgG functionalities for R1MAb's activities, we utilized two types of modifications. A dual mutation (D265A/N297A; DANA) in the Fc region abolishes binding to FcγRs and recruitment of immune effector cells by an IgG molecule (Gong et al., 2005). Neither the agonistic nor anti-diabetic activity of R1MAb2 was affected by the introduction of the DANA mutations; therefore the effector function plays no role in anti-diabetic activity of R1MAb2 (FIG. 9A-C). However, an engineered one-armed (OA) version of R1Mab1 (Atwell et al., *J. Mol. Biol.* 270:26-35 (1997)), lacking one of the Fab fragments (OA-R1MAb1) (FIGS. 9A and D) showed diminished agonistic activity (FIGS. 9E and F) and failed to reduce blood glucose, body weight, and hepatic and serum lipid levels db/db mice (FIGS. 9G and H), indicating that both the agonistic and anti-diabetic activities of R1MAbs are dependent on Ab bivalency (although we also test bispecific antibodies with only one anti-FGFR1 arm (e.g., with an anti-beta-Klotho arm) and confirm that they retain the beneficial attributes of the bivalent anti-FGFR1 R1MAbs). These correlations strongly suggest that R1MAb-induced activation of the signaling pathway downstream of FGFR1 likely mediates its anti-diabetic effects.

MAbs have emerged as a powerful therapeutic modality for the treatment of a number of human diseases. Our demonstration of potent anti-hyperglycemic and lipid-lowering activities of anti-FGFR1 agonistic MAb opens up a novel path towards development of therapeutic MAbs targeting FGFR1 or FGFR1-containing receptor complex for the treatment of type 2 diabetes and other obesity-related chronic disorders. MAb-based targeting of FGFR1 offers several favorable properties over recombinant FGF21 therapy. First, by their nature, MAbs provide predictable, modulatable, and far superior pharmacokinetics compared to FGF21 or any other nonantibody therapeutic protein. Indeed, we demonstrated that a single i.p. injection at 1-3 mpk of R1MAb1 or R1Mab2 into db/db mice leads to a remarkably sustained amelioration of hyperglycemia for over 30 days (FIGS. 2 and 5). Such a long-lasting glycemic effect has never been reported for any of the previously described anti-diabetic agents.

Example 3

Importance of Adipose Tissues in Diabetic Action of R1MAb and FGF21

Figure 10:
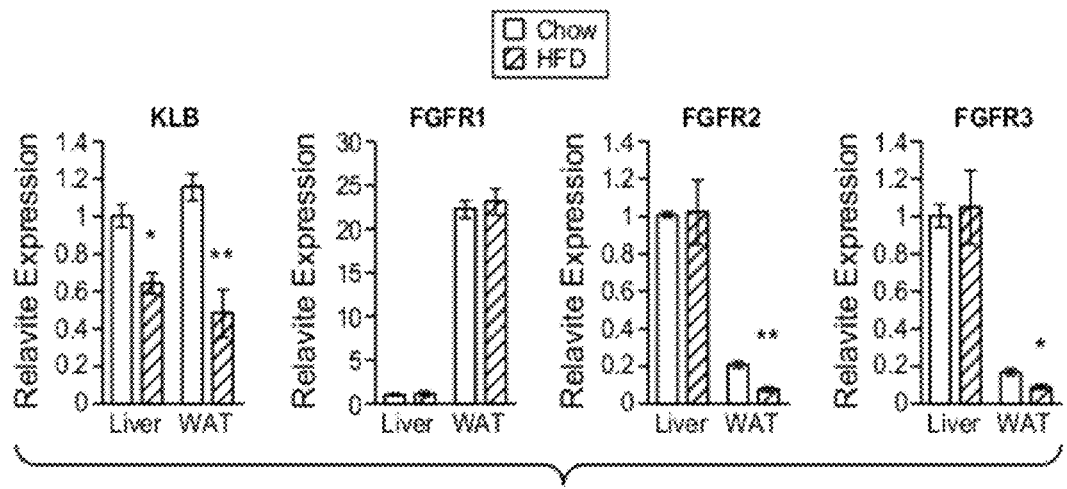
FIG. 10 shows mRNA expression of KLB and FGFR isoforms in liver and WAT. Chow-fed and HFD-fed C57BL/6 mice were 25 weeks old. HFD-fed mice were on HFD for 21 weeks. $*p<0.05$ or $**p<0.001$. N=6.
Figure 15:
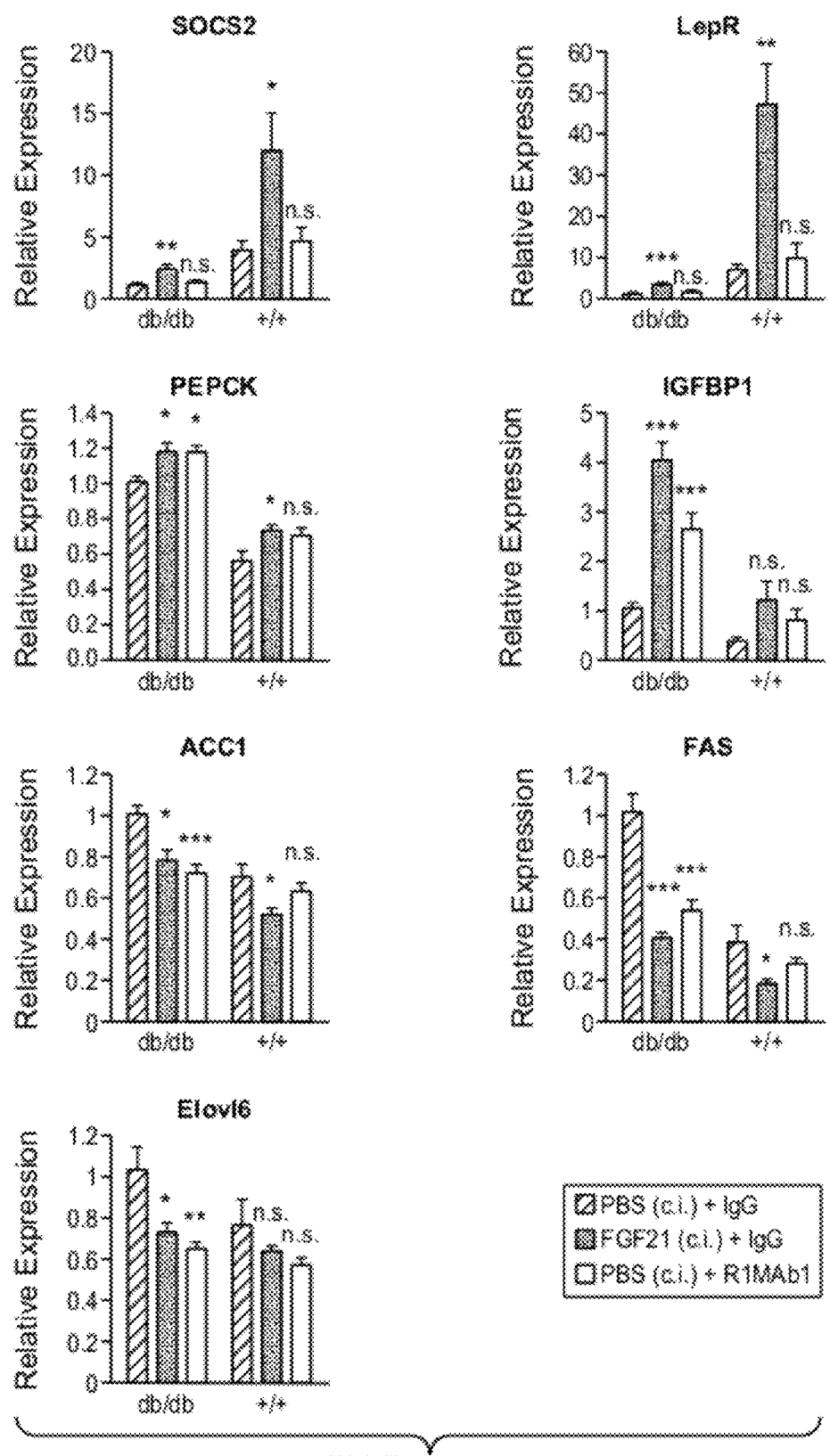
FIG. 15 shows gene expression analysis using mRNA isolated from liver tissue of the mice used in FIGS. 2C and 14A-14C. Tissue samples were isolated on day 5 after 4 h fast. Data represent mean±SEM with n=6 mice per group; *p<0.05, ***p<0.001 vs. PBS (c.i.)+IgG control, by two-tailed unpaired student's t-test (n.s.=not significant).

Recombinant FGF21 has been suggested to improve insulin sensitivity through adipose tissues and the liver (Berglund et al., *Endocrinology* 150:4084-93 (2009); Li et al., *FEBS Letters* 583:3230-34 (2009)). FGF21 injection into mice induced MEK and ERK phosphorylation in four KLB-expressing tissue types, the liver, white adipose tissue (WAT), brown adipose tissue (BAT), and pancreas, as previously reported (FIG. 3A, top) (Kurosu et al., *J. Biol. Chem.* 282: 26687-95 (2007); Xu et al., *Am. J. Physiol. Endocrinol. Metab.* 297(5): E1105-14 (2009)). In contrast, R1MAb1 injection leads to phosphorylation of the same downstream effectors in adipose tissues and pancreas, but not in the liver (FIG. 4A, bottom), consistent with very low FGFR1 mRNA expression in the liver (FIG. 10) (Fon Tacer et al., *Mol. Endocrinol.* 24(10): 2050-64 (2010)). Indeed, a side-by-side comparison of hepatic gene expression revealed that expression of two previously identified FGF21-targeted genes (leptin receptor (LepR) and suppressor of cytokine signaling 2 (SOCS2); Coskun et al., *Endocrinology* 149:6018-27 (2008), Inagaki et al., *Cell Metabolism* 8:77-83 (2008)) were induced by FGF21 but not by R1MAb1 (FIG. 15). On the other hand, hepatic expression of known insulin regulated genes (acetyl-CoA carboxylase 1 (ACCT), fatty acid synthase (FAS), elongase of long chain fatty acids family 6 (Elovl6), insulin-like growth factor (IGF)-binding protein (IGFBP)-1, phosphoenolpyruvate carboxykinase (PEPCK)) was similarly altered by both FGF21 and R1MAb1, suggesting that these genes might be regulated indirectly via hormonal (e.g. insulin) or metabolic changes. R1MAb1 markedly decreased hepatic and serum lipids when injected into db/db mice at day 7 post single injection, presumably due to lipid repartitioning effects through adipose tissues (FIG. 3B-D). R1MAb1 injection did not induce phosphorylation of MEK or ERK in lung and prostate (FIG. 3A), two cancer-prone tissue types that express FGFR1. These observations together suggest that adipose tissues, but not the liver, are central for the common metabolic activity of R1MAb and FGF21.

Figure 11:
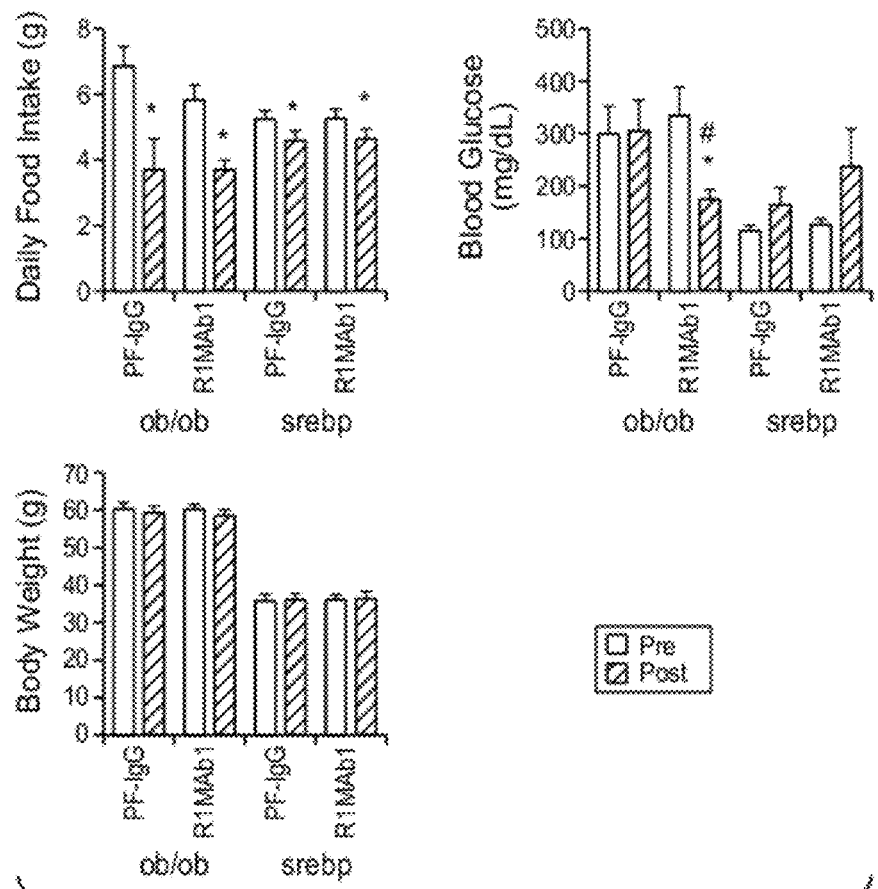
FIG. 11 shows the requirement for normal adipose function for the activity of FGF21 and R1MAb. Food intake (Top Left), blood glucose (Top Right), and body weight (Lower Left) of ob/ob or ap2-srebp1c transgenic mice after a single i.p. injection of R1Mab1 or control IgG at 1 mpk doses on day 0. The same mice described in FIG. 3E. N=7. $\#p<0.001$ (vs IgG), $*p<0.001$ (vs PF-IgG). The post treatment measurement was done at 1 day post injection.

To further investigate this point, we used lipoatrophic ap2-srebp1c transgenic mice, which display severe insulin resistance, leptin deficiency, and hepatomegaly, due to the lack of white adipose tissues and compromised brown adipose function (FIG. 3E, 11) (Shimomura et al., *Genes Dev.* 12:3182-94 (1998); Shimomura et al., *Nature* 401:73-76 (1999)). Consistent with the idea that normal adipose tissue function is required for the metabolic activity of R1MAb1, a single i.p. injection at 1 mpk improved HOMA-IR and glucose tolerance only in the control ob/ob mice but not in ap2-srebp1c mice (FIG. 3E). Food intake was reduced by R1MAb1 injection in both ob/ob mice and ap2-srebp1c transgenic mice, when compared to pair-fed mice injected with control IgG (FIG. 3E). In addition, continuous infusion of recombinant FGF21 also failed to improve insulin tolerance in ap2-srebp1c mice, although significant increase in serum β-hydroxybutyrate (i.e. ketone body) and decrease in cholesterol were observed (FIG. 3F).

Example 4

PGC1-Alpha Activation in Brown Adipose by R1MAb

Figures 1, 4A:
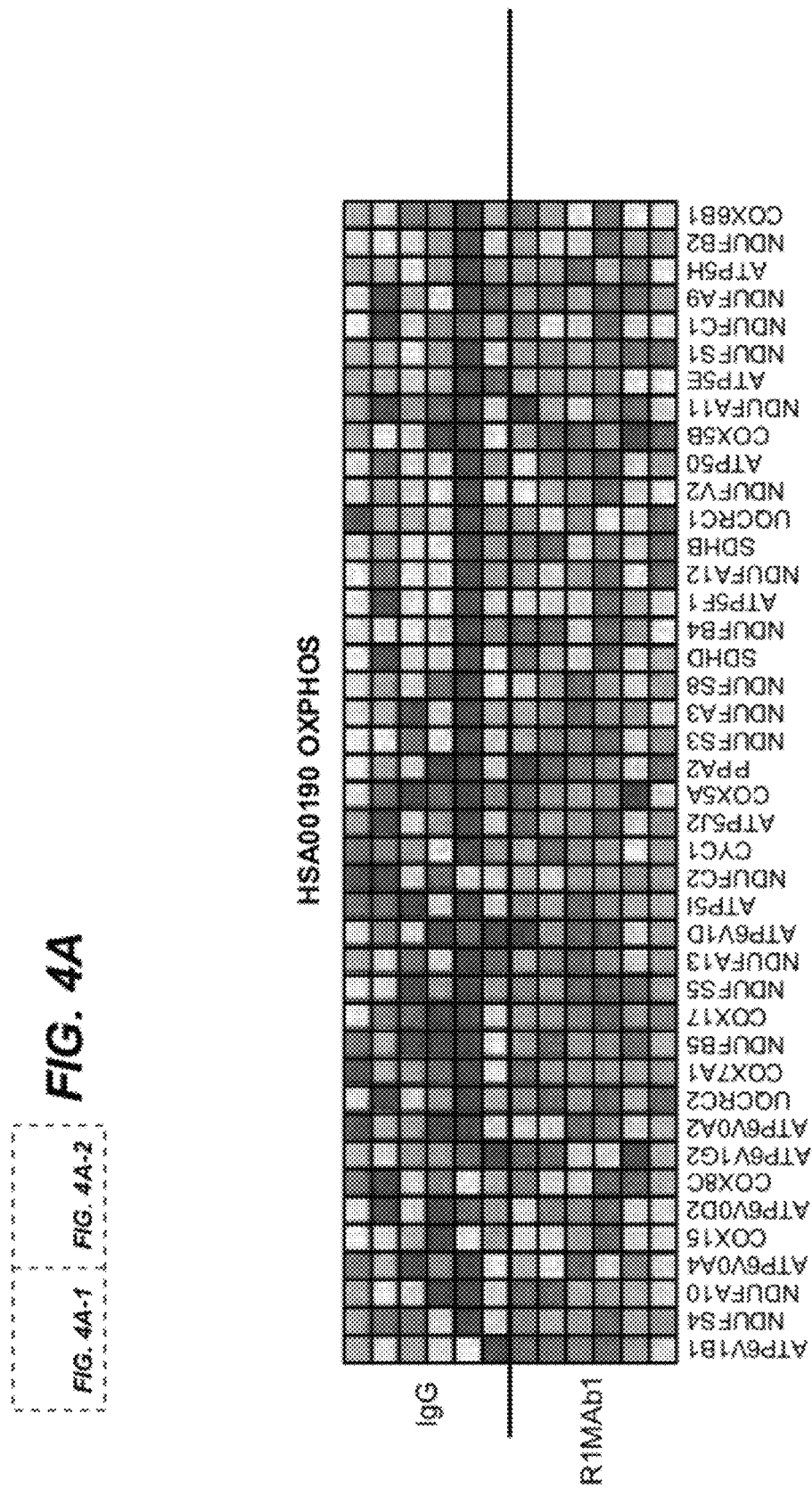
Figures 2, 4A:
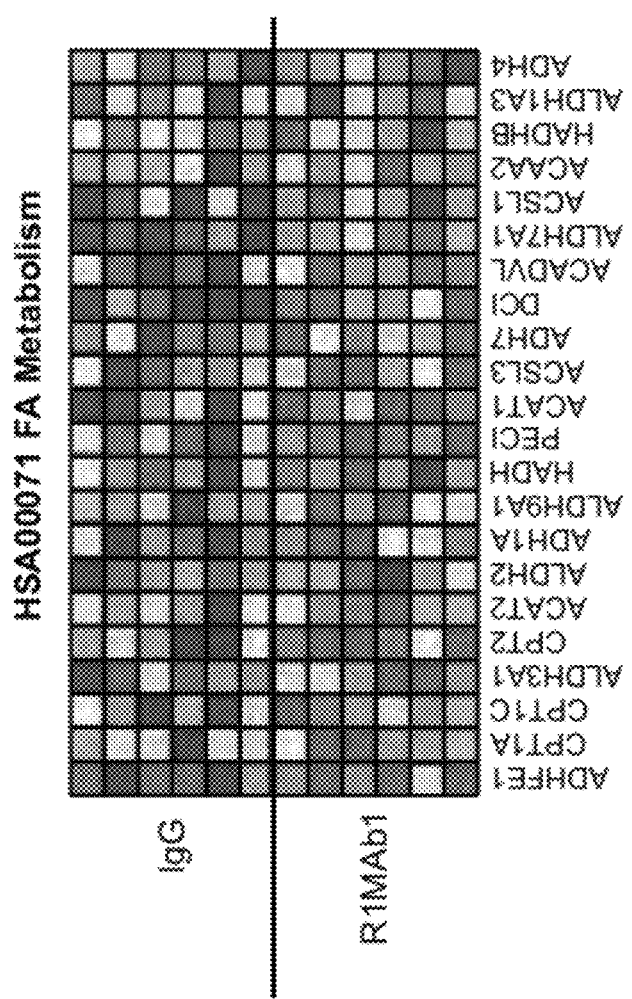
Figure 4B:
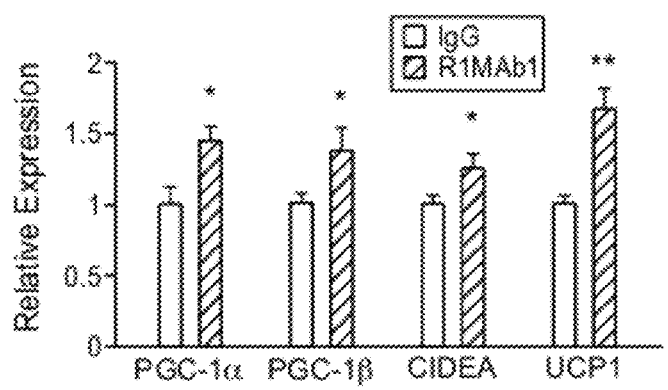
FIG. 4B shows mRNA expression in BAT by qPCR. N=6, $*p<0.05$, $**p<0.001$.
Figure 16:
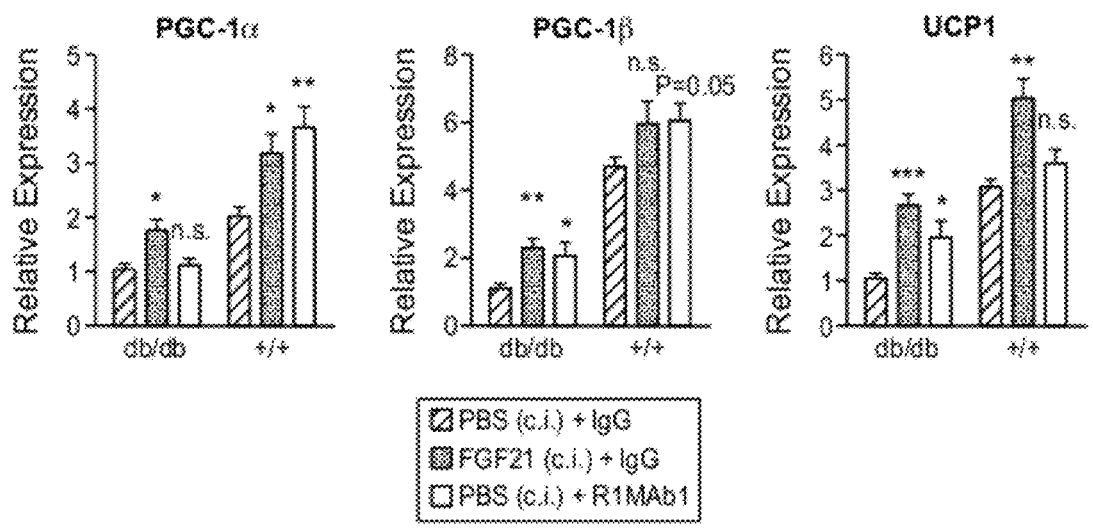
FIG. 16 shows gene expression analysis using mRNA isolated from brown adipose tissue of the mice used in FIGS. 2C, 14A-14C and 15. Tissue samples were isolated on day 5 after 4 h fast. Data represent mean±SEM with n=6 mice per group; *p<0.05, ***p<0.001 vs. PBS (c.i.)+IgG control, by two-tailed unpaired student's t-test (n.s.=not significant).

FGF21 has recently been suggested to activate the nuclear receptor transcriptional coactivator PGC-1α protein in adipose tissues and the liver to induce expression of the downstream genes associated with oxidative metabolism (Chau et al., *Proc. Nat'l. Acad. Sci. USA* 107:12553-58 (2010); Hondares et al., *Cell Metabolism* 11:206-12 (2010); Potthoff et al. *Proc. Nat'l. Acad. Sci. USA* 30; 106(26): 10853-8 (2009)). Indeed, when injected into ob/ob mice, R1MAb1 significantly increased BAT expression of genes involved in OXPHOS, and fatty acid metabolism as revealed by DNA microarray analysis followed by a gene-set enrichment analysis (FIG. 4A). R1MAb1 (and FGF21) also increased expression of PGC-1α, PGC-1β, and their major targets CIDEA and UCP1 in brown adipose tissues (measured by qPCR; FIGS. 4B and 16).

Figure 4C:
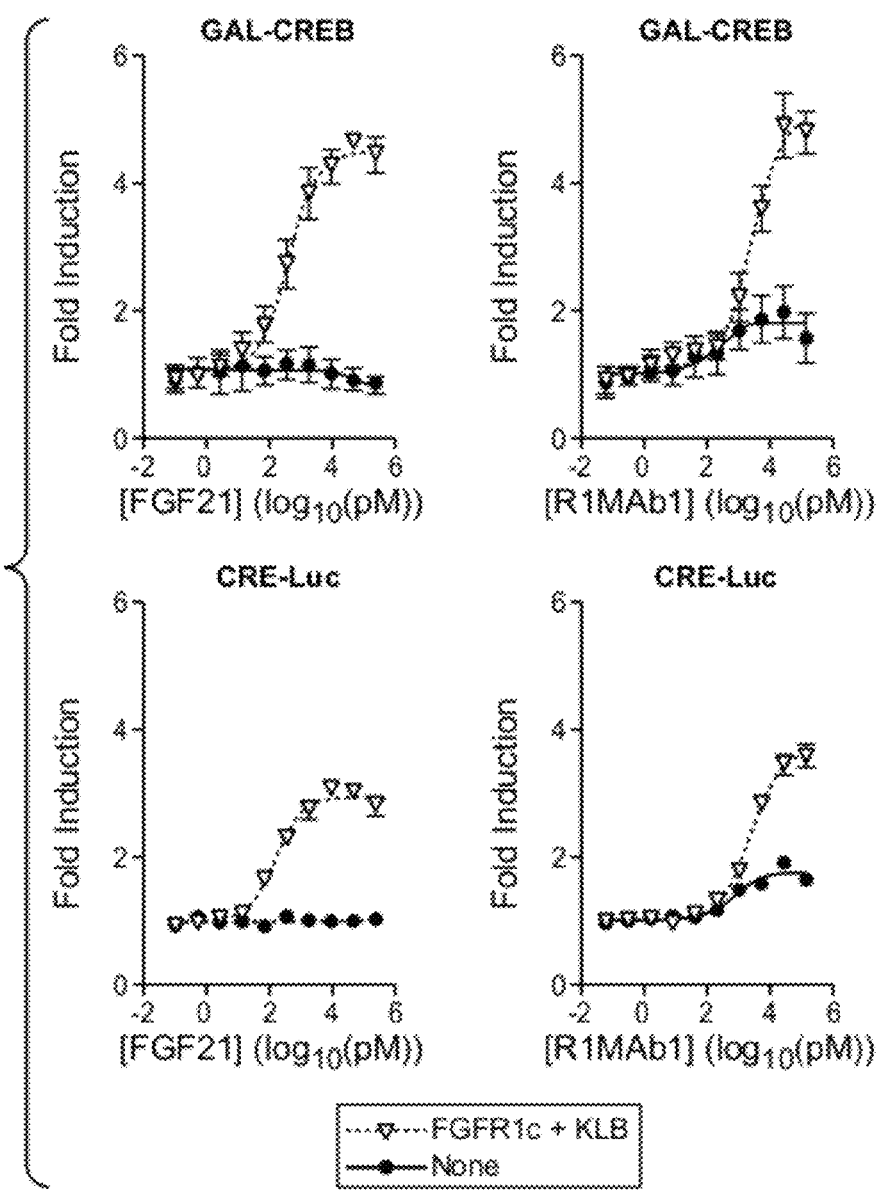
FIG. 4C shows a luciferase assay in HEK293 cells. The graph shows that both FGF21 and R1MAb1 induce transcription of a UAS-driven luciferase reporter gene in HEK293 cells through CREB fused to GAL4 DNA binding domain (GAL-CREB) (left two panels), or of a CRE-driven luciferase reporter gene (right two panels), in a dose-dependent manner. Some cells were also cotransfected to express FGFR1c and KLB (red; top curve in graphs). The results represent the average of triplicate experiments for the luciferase activity normalized by renilla activity.
Figure 4D:
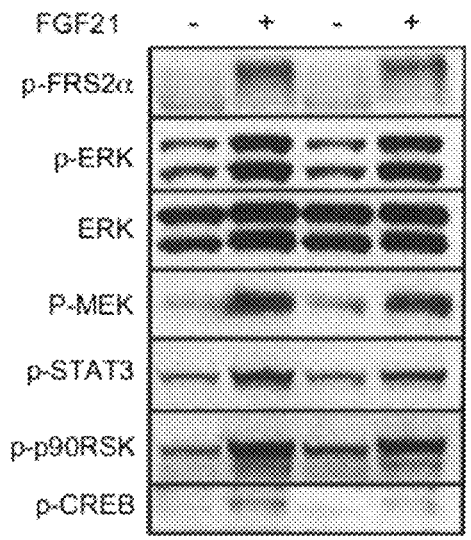
FIG. 4D shows WAT harvested 15 minutes after i.v. injection with 25 µg of FGF21 (+) or PBS (−), and subjected to western blot analysis.
Figure 4E:
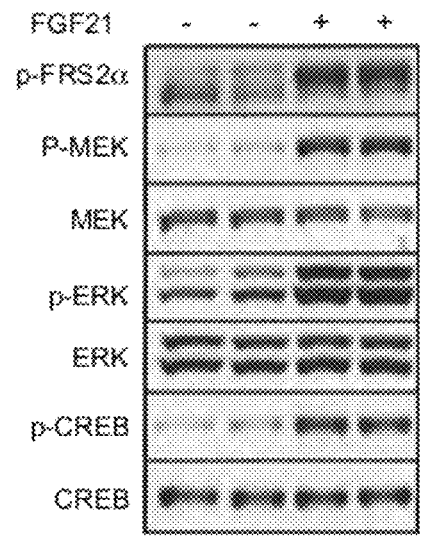
FIG. 4E shows western blot analysis of differentiated primary human adipocytes treated with FGF21 at 1 µg/ml for 30 minutes.
Figure 4F:
FIG. 4F shows a model for the signaling pathway through which FGF21 and R1MAb activates the PGC-1alpha program in adipose tissues.
Figure 12A:
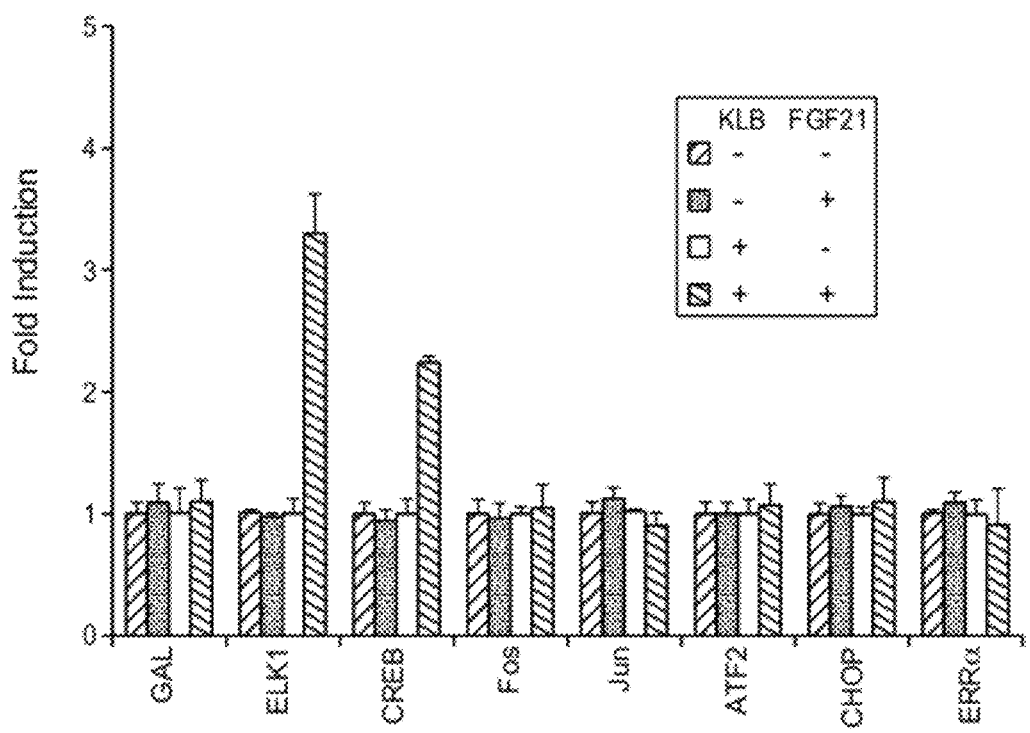
FIG. 12A shows a cell-based luciferase assay in HEK293. Cells were cotransfected with an expression vectors for an indicated GAL-fusion proteins, SV40-renilla Luciferase, and GAL-responsive luciferase reporter. Some cell were also cotransfected with expression vector for KLB as indicated. The transfected cells were incubated with media containing conditioned medium from HEK293 cells transfected with expression vector for FGF21 or control empty vector as indicated. After 6 hours of incubation, cells were subjected to luciferase assays. Transcriptional activation was assessed by the relative firefly luciferase activity normalized by renilla luciferase activity and expressed as fold induction.
Figure 12B:
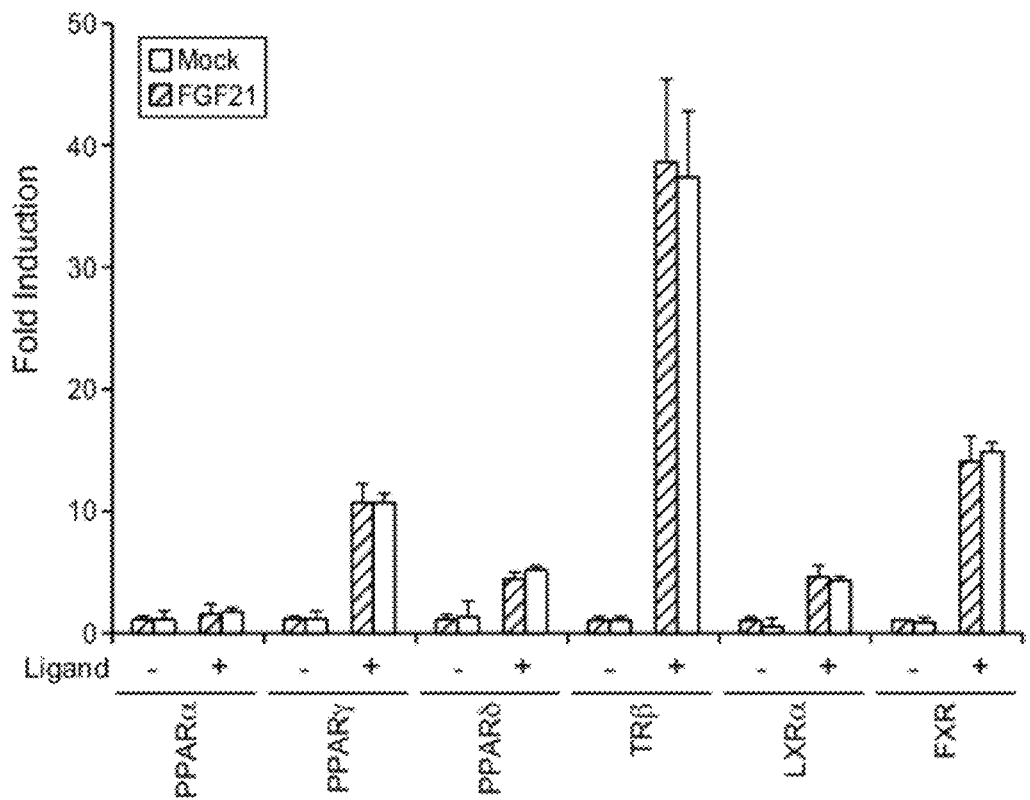
FIG. 12B shows a similar luciferase assay where some cells were cotreated with the following nuclear receptor ligand: 1 MM Wy14643 (PPARα), 5 nM GW101516 (PPARδ), 50 nM rosiglitazone (PPARγ), 50 nM T0901317 (LXRα), 5 nM T3 (TRβ), 30 MM CDCA (FXR). Note that FGF21 did not affected activity of any of the nuclear receptors tested here with or without cognate ligand treatment.
Figure 12C:
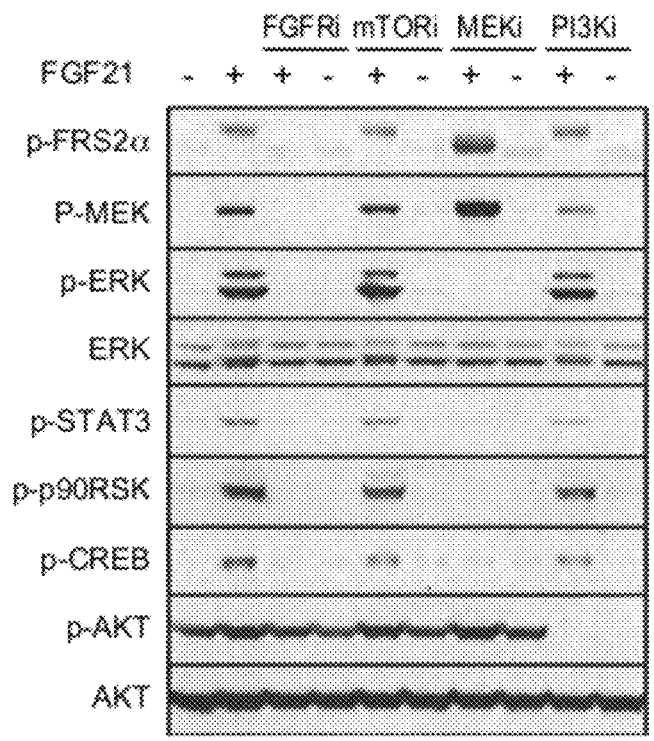
FIG. 12C shows western blot analysis of HEK293 cells treated with FGF21 at 0.5 μg/ml for 10 minutes. Some cells were pretreated with an inhibitor for FGFR (100 nM PD173074), mTOR (100 nM rapamycin) MEK1/2 (10 μM U0126), PI3K (1 μM wortmannin) as indicated.
Figure 12D:
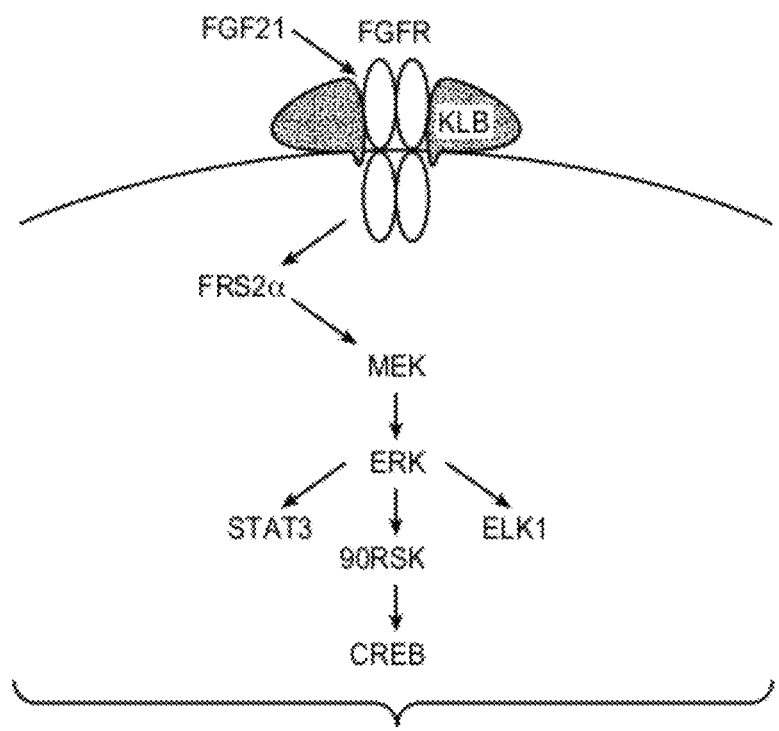
FIG. 12D shows downstream genes involved in oxidative metabolism in adipose tissues.
Figure 13:
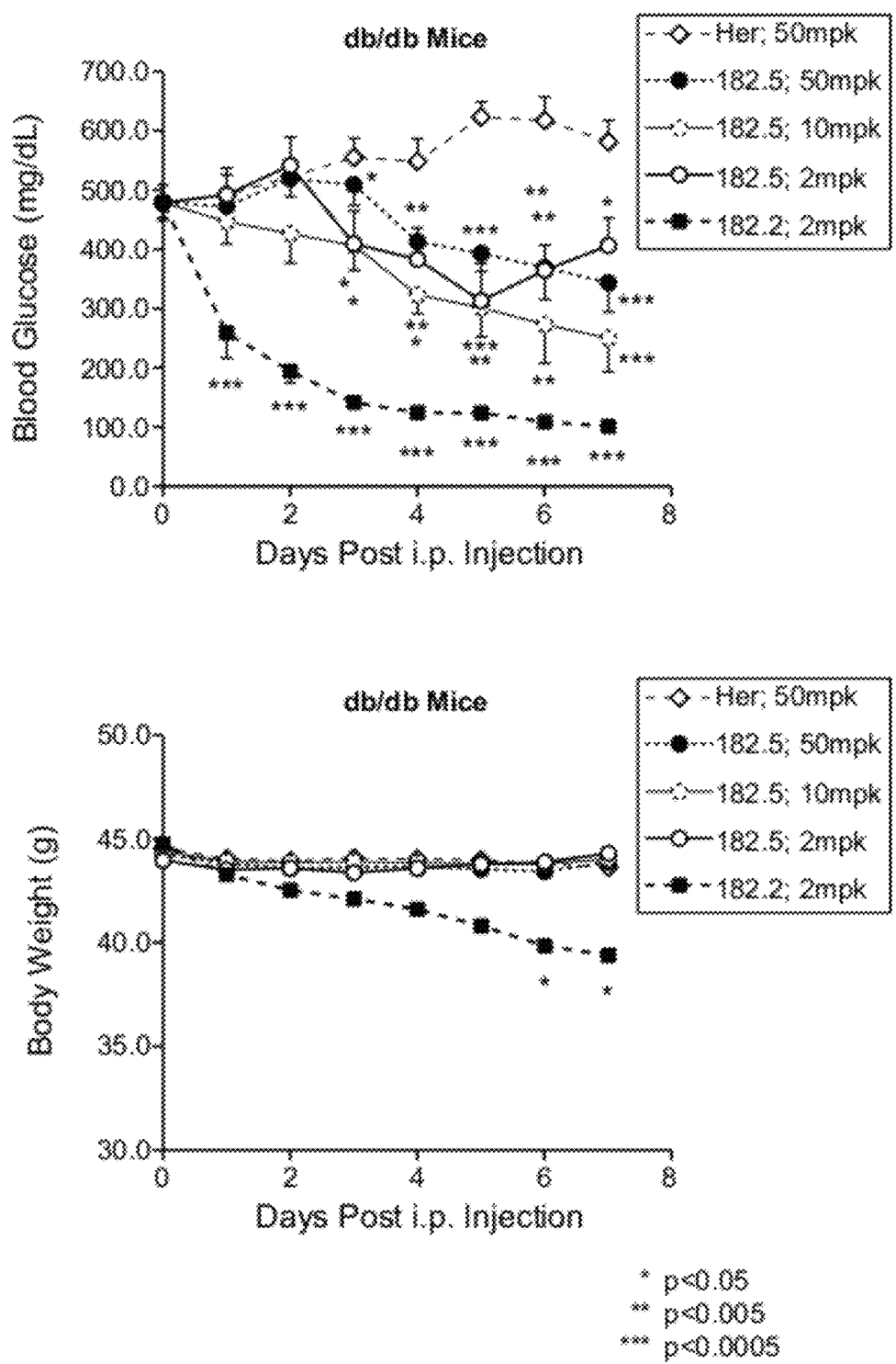
FIG. 13 shows blood glucose (top) and body weight (bottom) of db/db mice after a single i.p. injection of R1MAb2 (labeled as 182.2), R1MAb3 (labeled as 182.5) or control IgG (anti-Her2) at indicated doses. N=6, *p<0.05, p<0.005, *p<0.0005. R1MAb3 comprises VH comprising SEQ ID NO: 6 and VH comprising SEQ ID NO: 4.
Figure 14A:
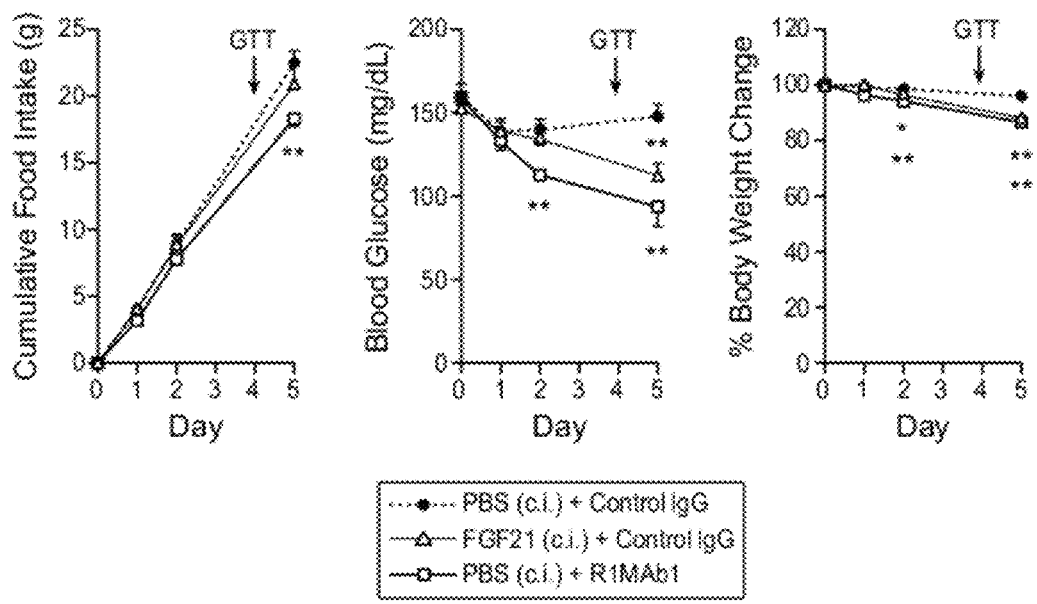
FIG. 14A shows cumulative food intake, blood glucose, and body weight change of lean C57BL/6 mice after a single intraperitoneal injection of R1MAb1 or control IgG at 0.5 mpk. The mice were also implanted subcutaneously with an osmotic mini-pump on day 0 to continuously infuse (c.i.) recombinant FGF21 at 1.2 mpk/day or vehicle control (PBS). On day 3, the mice were overnight fasted to conduct glucose tolerance test (GTT) on day 4 (arrow).
Figure 14B:
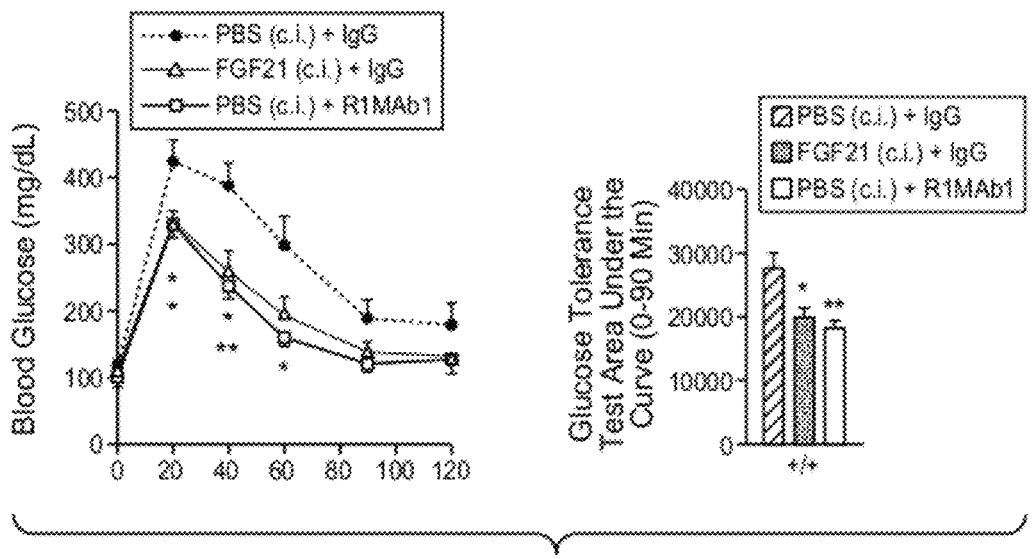
FIG. 14B shows glucose tolerance tests conducted with 2 g/kg glucose injected intraperitoneally on day 4 after an overnight fast.
Figure 14C:
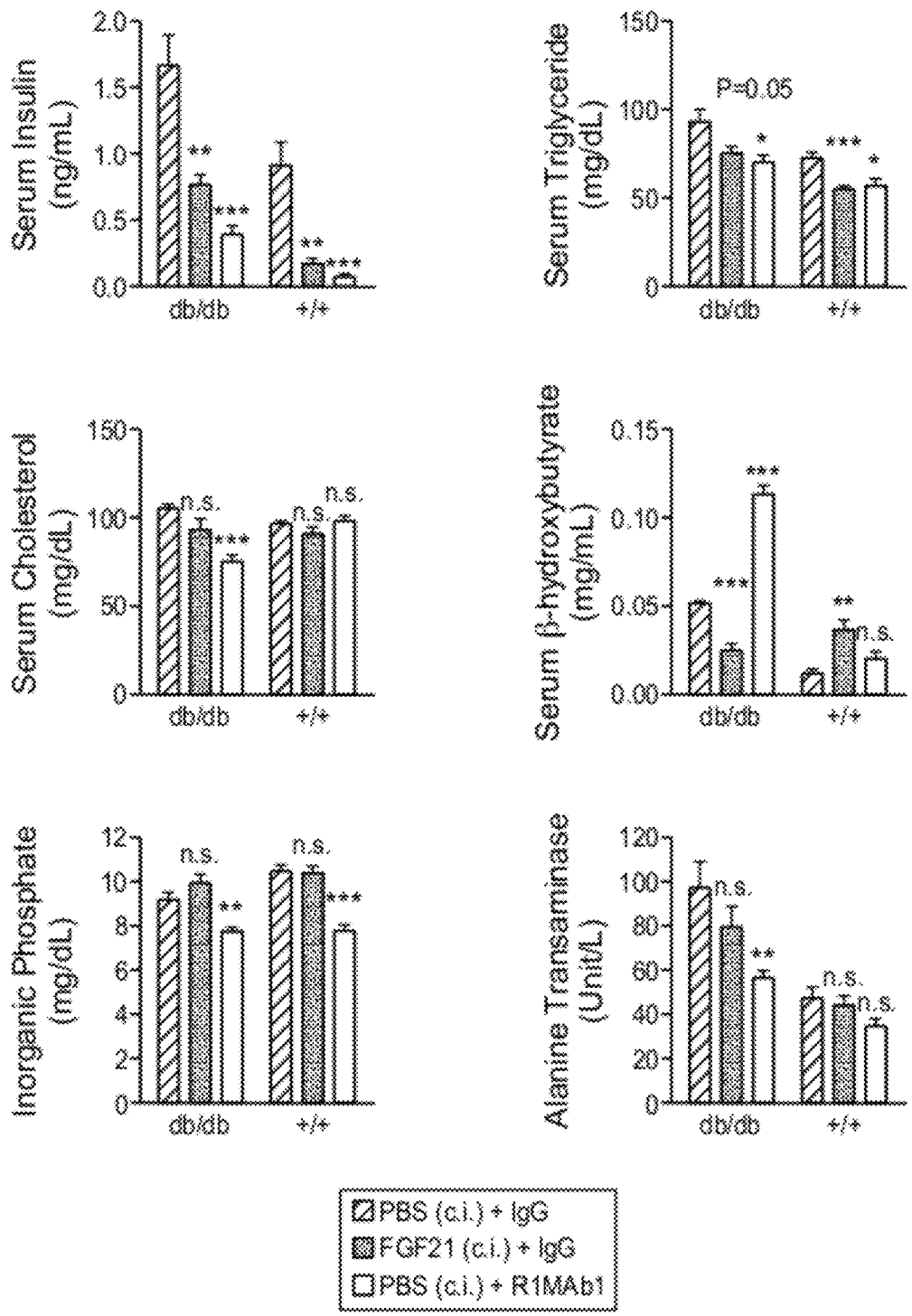
FIG. 14C shows serum analysis of mice shown in FIGS. 2C, 14A and 14B. Serum samples were collected at day 5 after 4 h fast. Data represent mean±SEM with n=6 mice per group; *p<0.05, p<0.01, *p<0.001 vs. PBS (c.i.)+IgG control, by two-tailed unpaired student's t-test (n.s.=not significant).

Transcription of PGC-1α is regulated through cAMP Response Elements (CREs) in the promoter region and the CREB transcription factor that binds to the CREs (Herzig et al., *Nature* 413:179-83 (2001); Karamitri et al., *J. Biol. Chem.* 284:20738-52 (2009); Muraoka et al., *Am. J. Physiol. Endocrinol. Metab.* 296:E1430-39 (2009); Shi et al., *J. Biol. Chem.* (2005)). In a screen to identify metabolism-related transcription factors that can be activated by FGF21 in HEK293 cells expressing KLB, we found that GAL-CREB fusion protein can be activated by FGF21 (FIGS. 12A-12B). Subsequently, we found that both FGF21 and R1MAb1 can activate GAL-CREB reporter as well as CRE-luciferase reporter in a dose dependent fashion in HEK293 cells (FIG. 4C). Consistent with the idea that CREB functions as a downstream effector, FGF21 increased the phosphorylation of CREB and p90RSK, an upstream CREB kinase regulated by ERK, in mouse white adipose tissues (FIG. 4D), differentiated human primary adipocyte (FIG. 4E), and HEK293 cells (FIG. 12C). Thus, CREB activation by FGF21 and R1MAb likely contributes to induction of PGC-1alpha and a set of downstream genes involved in oxidative metabolism in adipose tissues (FIGS. 4F and 12D). In addition to transcriptional regulation suggested here, FGF21 has been reported to activate PGC-1α post-translationally via activation of AMPK (Chau et al., supra), although we failed to observe evidence of AMPK activation in vitro or in vivo by R1MAb (data not shown). Collectively, our results support the role of PGC-1α in adipose tissues in mediating the anti-lipid and anti-diabetic effects of FGF21 and R1MAb.

Example 5

Testing Bispecific Anti-FGFR1/Anti-Beta-Klotho Antibodies

Another important difference between our R1MAbs and FGF21 is target receptor specificity. FGF21 can act on FGFR1c, 2c, and 3c, but its effects are likely limited to KLB expressing tissues (i.e. liver, adipose, and pancreas) (Fon Tacer et al., supra; Kurosu et al., *J. Biol. Chem.* 282:26687-95 (2007); Ogawa et al., *Proc. Nat'l. Acad. Sci. USA* 104:7432-37 (2007)). In contrast, the target tissues of our R1MAbs are determined by the expression of FGFR1 and tissue distribution of the antibody molecule, but unlikely limited by KLB expression. Indeed, we observed mild hypophosphatemia in mice treated with R1MAb1, suggesting the activation of FGF23/Klotho-pathway in the kidney. Accordingly, we generated bispecific anti-KLB/FGFR1 bispecific antibodies using phage display or hybridoma technology (BALBc mice immunized with HEK293 cells expressing FGFR1c and KLB) to generate separate anti-KLB antibodies and knob-and-hole technology (Merchant et al. *Nature Biotechnol.* 16(7): 677-81 (1998)). We tested the ability of these bispecific antibodies to activate GAL-Elk1 expression and confirmed that these antibodies depend on the presence of both beta-Klotho and FGFR1 for downstream signal activation. We also confirmed that one of the antibodies could increase phosphorylation of downstream signaling intermediates, MEK and ERK ½ in differentiated primary human adipocytes. One of the bispecific antibodies cross reacts with the murine proteins and we used this antibody to test the in vivo activity of a bispecific antibody. We observed that this bispecific antibody reduced blood glucose levels without elevating serum FGF23, whereas the corresponding control anti-FGFR1 (monospecific) antibody reduced blood glucose levels to a similar extent but significantly elevated serum FGF23 levels.

Next we test the ability of these bispecific antibodies to provide the metabolic benefits of the anti-FGFR1 agonistic antibodies. We generate transgenic mice expressing human beta-Klotho (the R1MAb1 and R1MAb2 each recognize murine FGFR1) and confirm that the anti-KLB/FGFR1 bispecific antibodies described above improve glucose tolerance in mouse models, e.g. high-fat diet fed hKLB transgenic mice. We also generate anti-beta-Klotho antibodies that react with the protein in other model animals (e.g. rat, rabbit, cynomologous and rhesus monkeys) and similarly test the ability of bispecific antibodies constructed with these and the anti-FGFR1 antibodies to provide metabolic benefits.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An anti-fibroblast growth factor receptor-1 (FGFR1) antibody, wherein the antibody binds to peptide #26 KLHAVPAAKTVKFKCP (SEQ ID NO: 28) or peptide #28 FKPDHRIGGYKVRY (SEQ ID NO: 29) and wherein the antibody is a human, humanized, or chimeric antibody.

2. An anti-FGFR1 antibody, wherein the antibody comprises (a) HVR-H1 comprising the amino acid sequence GFTFTSNWIS (SEQ ID NO: 9), (b) HVR-H2 comprising an amino acid sequence selected from the group consisting of AEIDPYDGATDYADSVKG (SEQ ID NO: 14) and EIDPYDGATDYADSVKG (SEQ ID NO: 15), and (c) HVR-H3 comprising an amino acid sequence selected from the group consisting of TGTDVMDY (SEQ ID NO: 19) and GTDVMDY (SEQ ID NO: 20).

3. The antibody of claim 2, further comprising (a) HVR-L1 comprising the amino acid sequence RASQDVSTAVA (SEQ ID NO: 21); (b) HVR-L2 comprising the amino acid sequence SASFLYS (SEQ ID NO: 22); and (c) HVR-L3 comprising the amino acid sequence QQSYTTPPT (SEQ ID NO: 23).

4. The antibody of any one of claims 1, 2 and 3, wherein the antibody is a multispecific antibody.

5. The antibody of claim 4, wherein the antibody also binds to beta-Klotho.

6. The antibody of any one of claims 1, 2, and 3, which is an IgG1 antibody.

7. The antibody of claim 4, which is an IgG1 antibody.

8. The antibody of claim 5, which is an IgG1 antibody.

9. A pharmaceutical formulation comprising an antibody of any one of claims 1, 2, and 3 and a pharmaceutically acceptable carrier.

10. A pharmaceutical formulation comprising an antibody of claim 4 and a pharmaceutically acceptable carrier.

11. A pharmaceutical formulation comprising an antibody of claim 5 and a pharmaceutically acceptable carrier.

12. A pharmaceutical formulation comprising an antibody of claim 6 and a pharmaceutically acceptable carrier.

13. A pharmaceutical formulation comprising an antibody of claim 7 and a pharmaceutically acceptable carrier.

14. A pharmaceutical formulation comprising an antibody of claim 8 and a pharmaceutically acceptable carrier.

* * * * *